US005811428A

United States Patent [19]
Suto et al.

[11] Patent Number: 5,811,428
[45] Date of Patent: Sep. 22, 1998

[54] PYRIMIDINE CARBOXAMIDES AND RELATED COMPOUNDS AND METHODS FOR TREATING INFLAMMATORY CONDITIONS

[75] Inventors: Mark J. Suto; Mark E. Goldman; Leah M. Gayo; Lynn J. Ransone-Fong, all of San Diego; Moorthy S. S. Palanki, Encinitas; Robert W. Sullivan, Oceanside, all of Calif.

[73] Assignee: Signal Pharmaceuticals, Inc., San Diego, Calif.

[21] Appl. No.: 581,473

[22] Filed: Dec. 18, 1995

Related U.S. Application Data

[60] Provisional application No. 60/003,109 Sep. 1, 1995.
[51] Int. Cl.⁶ ................ A61K 31/505; C07D 239/36
[52] U.S. Cl. ............ 514/256; 514/269; 514/274; 514/275; 544/242; 544/298; 544/316; 544/322; 544/334; 544/335
[58] Field of Search ................ 514/256, 269, 514/274, 275; 544/298, 316, 322, 332, 334, 335

[56] References Cited

U.S. PATENT DOCUMENTS

| | | | |
|---|---|---|---|
| 3,517,009 | 6/1970 | Kim et al. | 260/256.4 |
| 3,517,010 | 6/1970 | Kime et al. | 260/256.4 |
| 3,845,055 | 10/1974 | Hoegerle | 260/256.4 |
| 4,115,575 | 9/1978 | Frei et al. | 424/250 |
| 4,195,090 | 3/1980 | Frei et al. | 424/263 |
| 4,250,178 | 2/1981 | Bucher et al. | 424/251 |
| 4,410,530 | 10/1983 | Frei et al. | 424/251 |
| 4,734,418 | 3/1988 | Yokoyama et al. | 514/258 |
| 4,965,270 | 10/1990 | Harnden et al. | 514/262 |
| 5,250,548 | 10/1993 | Winn et al. | 514/340 |
| 5,397,781 | 3/1995 | Yanagibashi et al. | 514/256 |

FOREIGN PATENT DOCUMENTS

| | | |
|---|---|---|
| A-38554/93 | 11/1993 | Australia . |
| 489416 | 6/1949 | Belgium . |
| 475 206 A2 | 3/1992 | European Pat. Off. . |
| 569 912 A1 | 11/1993 | European Pat. Off. . |
| 2139411 A | 1/1973 | France . |
| 2906461 A1 | 8/1979 | Germany . |
| 3205638 A | 8/1983 | Germany . |
| 77-83679 B | 7/1977 | Japan . |
| 61-249973 A | 11/1986 | Japan . |
| 63-107966 A | 5/1988 | Japan . |
| 63-198670 A | 8/1988 | Japan . |
| 1-180804 A | 7/1989 | Japan . |
| 1-180805 A | 7/1989 | Japan . |
| WO 95/25723 | 9/1995 | WIPO . |

OTHER PUBLICATIONS

Brasier et al., "Optimized Use of the Firefly Luciferase Assay as a Reporter Gene in Mammalian Cell Lines," *BioTechniques* 7(10): 1116–1122, 1989.

Ghosh et al. "Structure of NF–κB p50 homodimer bound to a κB site," *Nature* 373: 303–310, 1995.

Santerre et al., "Use of Vectors to Confer Resistance to Antibiotics G418 and Hygromycin in Stably Transfected Cell Lines," *Methods in Molecular Biology* 7:245–256, 1991.

Sen and Baltimore, "Inducibility of κ immunoglobulin enhancer–binding protein NF–κ B by a posttranslational mechansim," *Cell* 47(6):921–928, 1986.

Su et al., "JNK Is Involved in Signal Integration during Costimulation of T Lymphocytes," *Cell* 77:727–736, 1994.

Carlson, R., "Pulmonary–Allergy, Dermatological, Gastrointestinal & Arthritis. Newer immunosuppressive drugs and other agents for the treatment of rheumatoid arthritis—An update," *Exp. Opin. Invest. Drugs* 4(9):853–859, 1995.

Dostert et al., "Studies on the neuroleptic benzamides. I.–Synthesis and antidopaminergic properties of new pyrimidine derivatives," *Eur. J. Med. Chem. —Chim. Ther.* 17(5):437–444, 1982.

Dostert et al., "Studies on the neuroleptic benzamides. III.–Synthesis and antidopaminergic properties of new 3–nortropane derivatives," *Eur. J. Med. Chem.—Chim. Ther.* 19(2):105–110, 1984.

Kanatomo et al., "Sparsomycin Analogs. IV. Synthesis and Antitumor Avtivity of Pyrimidine–5–carboxamides and (E)–β–(Pyrimidin–5–yl)–acrylamides," *Chem. Pharm. Bull.* 36(6):2042–2049, 1988.

Dlugosz, A., "The reaction of 4–mercaptopyrimidines with 2–(2'–aminoethylamino)ethanol," *Die Pharmazie* 47(3): 186–188, 1992.

Prystaš and Šorm, "Nucleic Acids Components and Their Analogues. LXXXV. Synthesis of 5–Cyanouracil, 5–Nitrouracil, and 5–Aminouracil 1–Glycosyl Derivatives," *Collection Czechoslov Chem. Commun.* 31: 3990–4001, 1966.

Irwin et al., "Synthesis of Pyrido[3,2–d]pyrimidines from 5–Aminopyrimidines," *Journal of the Chemical Society C* 18: 1745–1750, 1967.

Krchnák and Arnold, "Novel Pyrimidine Derivatives, Reactions and Ultraviolet Spectra," *Collection Czechoslov. Chem. Commun.* 40: 1396–1402, 1975.

Bauér et al., "New Method for the Preparation of Unsubstituted Benzo[b]–and Naphtho[2,1–b]Thiophenes," *Chemistry of Heterocyclic Compounds* 19(1): 112–114, 1983.

Dostert et al., "Studies on the neuroleptic benzamides. I.–Synthesis and antidopaminergic properties of new pyrimidine derivatives," *Eur. J. Med. Chem. —Chim. Ther.* 17(5): 437–444, 1982.

*Primary Examiner*—Yogendra N. Gupta
*Attorney, Agent, or Firm*—Seed and Berry

[57] ABSTRACT

Compounds having utility as antinflammatory agents in general and, more specifically, for the prevention and/or treatment of immunoinflammatory and autoimmune diseases are disclosed. The compounds are pyrimidine- or pyrazine-containing compounds and, in one embodiment, are carboxyamides of the same. Methods are also disclosed for preventing and/or treating inflammatory conditions by administering to an animal in need thereof an effective amount of a compound of this invention, preferably in the form of a pharmaceutical composition.

27 Claims, 5 Drawing Sheets

PYRIMIDINE CARBOXAMIDES AND RELATED COMPOUNDS AND METHODS FOR TREATING INFLAMMATORY CONDITIONS

CROSS-REFERENCE TO RELATED APPLICATION

This application claims the benefit of application Ser. No. 60/003,109, filed Sep. 1, 1995.

TECHNICAL FIELD

The present invention relates generally to compounds that block intracellular signal transduction and activation of transcription factors, and to methods for preventing or treating immunoinflammatory and autoimmune diseases.

BACKGROUND OF THE INVENTION

Signals necessary for cell growth, differentiation, response to bioregulatory molecules, infectious agents and physiological stress involve changes in the rates of gene expression. The ability to respond appropriately to such signaling events challenge the survival of the cell and ultimately the organism. Perturbations in the normal regulation of these specific genetic responses can result in pathogenic events which lead to acute and chronic disease.

In certain autoimmune diseases or chronic inflammatory states, continuous activation of T-cells eventually leads to a self-perpetuating destruction of normal tissues or organs. This is caused by the induction of adhesion molecules, chemotaxis of leukocytes, activation of leukocytes and the production of mediators of inflammation. All of these events are regulated at the level of transcription for the production of new proteins, including cytokines. The production of cytokines, as well as a number of other cellular regulators, is controlled by a family of proteins known as transcription factors (TFs). These transcription factors, when activated, bind to specific regions on the DNA and act as molecular switches or messengers to induce or upregulate gene expression. The activation of these TFs is caused by a variety of external signals including physiological stress, infectious agents and other bioregulatory molecules. Once the plasma membrane receptors are activated, a cascade of protein kinases and second messengers are induced which, in turn, result in the production of RNA transcripts. The end result is the production of proinflammatory proteins via translation and processing of the RNA transcripts.

This activation system can, at times, be very robust. For example, a specific set of external signals could result in a single transcription factor to induce many proteins responsible for a given disease. Therefore, regulating this process by disrupting the production of activated TF(s) has the potential to attenuate the production of the associated pathological proteins, thereby halting or reversing the course of the disease.

Two transcription factors, NFκB and AP-1, have been shown to regulate the production of many proinflammatory cytokines and related proteins that are elevated in immunoinflammatory diseases. These TFs regulate interleukin-1 (IL-1), interleukin-2 (IL-2), tumor necrosis factor-α (TNFα), interleukin-6 (IL-6) and interleukin-8 (IL-8) levels in a variety of cell types. For example, NFκB and other related complexes are involved in the rapid induction of genes whose products function in protective and proliferative responses upon exposure of cells to external stimuli. Similarly, AP-1 has a significant role in the regulation of interleukin-2 (IL-2) and tumor necrosis factor-α (TNF-α) transcription during T-cell activation. In addition, TNF-α and IL-1 are strong activators of collagenase, gelatinase and stromelysin gene expression, which require a single AP-1 binding site in the promoter region of these genes. Therefore, an inhibitor of NFκB and/or AP-1 activation would coordinately repress the activities of a series of proteinases. In addition, cell adhesion molecules are also controlled by these TFs. All of these proteins have been shown to play a role in diseases, including osteoarthritis, transplant rejection, ischemia, reperfusion injury, trauma, certain cancers and viral disorders, and autoimmune diseases such as rheumatoid arthritis, multiple sclerosis, psoriasis, inflammatory bowel disease, glomerulonephritis, lupus and juvenile diabetes. In summary, the role of these TFs is to act as a transducer for certain stimuli that lead to immune, inflammatory, and acute phase responses.

Since many diseases are caused by the inappropriate production of proteins, conventional therapeutic approaches have focused on inhibiting function or activity of individual effector proteins. These treatments have not always proved to be effective and, at times, are associated with many undesirable side effects. Therefore, there is a need for new therapies for the prevention and/or treatment of immunoinflammatory and autoimmune diseases. More specifically, there is a need for compounds that prevent, preferably by inhibiting transcription at an early stage, the production of proteins associated with immunoinflammatory and autoimmune diseases. Furthermore, these compounds should inhibit the kinase(s) that regulate the activation of TFs such as NFκB and AP-1. The present invention fulfills these needs and provides further related advantages.

SUMMARY OF THE INVENTION

In brief, this invention is directed to compounds that block the activation of transcription factors (TFs), particularly NFκB and AP-1, and are believed to function through inhibition of a family of specific kinases. This results in a decrease in a number of proinflammatory proteins, including IL-1, IL-2, IL-8 and/or TNFα, which are responsible for tissue and organ damage associated with diseases such as rheumatoid arthritis, osteoarthritis, related autoimmune disorders and tissue rejection. Accordingly, compounds of the present invention are useful in, for example, the prevention of organ and tissue rejection associated with transplantation. Furthermore, the compounds of this invention also have utility in the prevention and/or treatment of immunoinflammatory and autoimmune diseases, as well as having general activity as anti-inflammatory agents.

In one embodiment of this invention, compounds are disclosed having the following general structure (I):

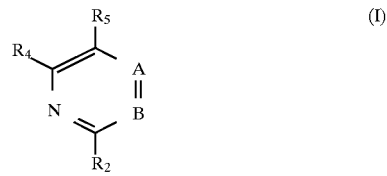

wherein A is C—$R_6$ when B is N, and A is N when B is C—$R_1$, and wherein $R_1$, $R_2$, $R_4$, $R_5$ and $R_6$ are as defined in the following detailed description.

In another embodiment, a pharmaceutical composition is disclosed containing one or more compounds of this invention in combination with a pharmaceutically or prophylactically acceptable carrier or diluent.

In a further embodiment, methods are disclosed for preventing and/or treating inflammatory conditions by administering to a warm-blooded animal in need thereof an effective amount of a compound of this invention. Such inflammatory conditions include both immunoinflammatory conditions and autoimmune diseases. In the practice of the disclosed methods, the compounds are preferably administered to the warm-blooded animal in the form of a pharmaceutical composition.

These and other aspects of this invention will become evident upon reference to the attached figures and the following detailed description.

DETAILED DESCRIPTION OF THE INVENTION

Figure 1:
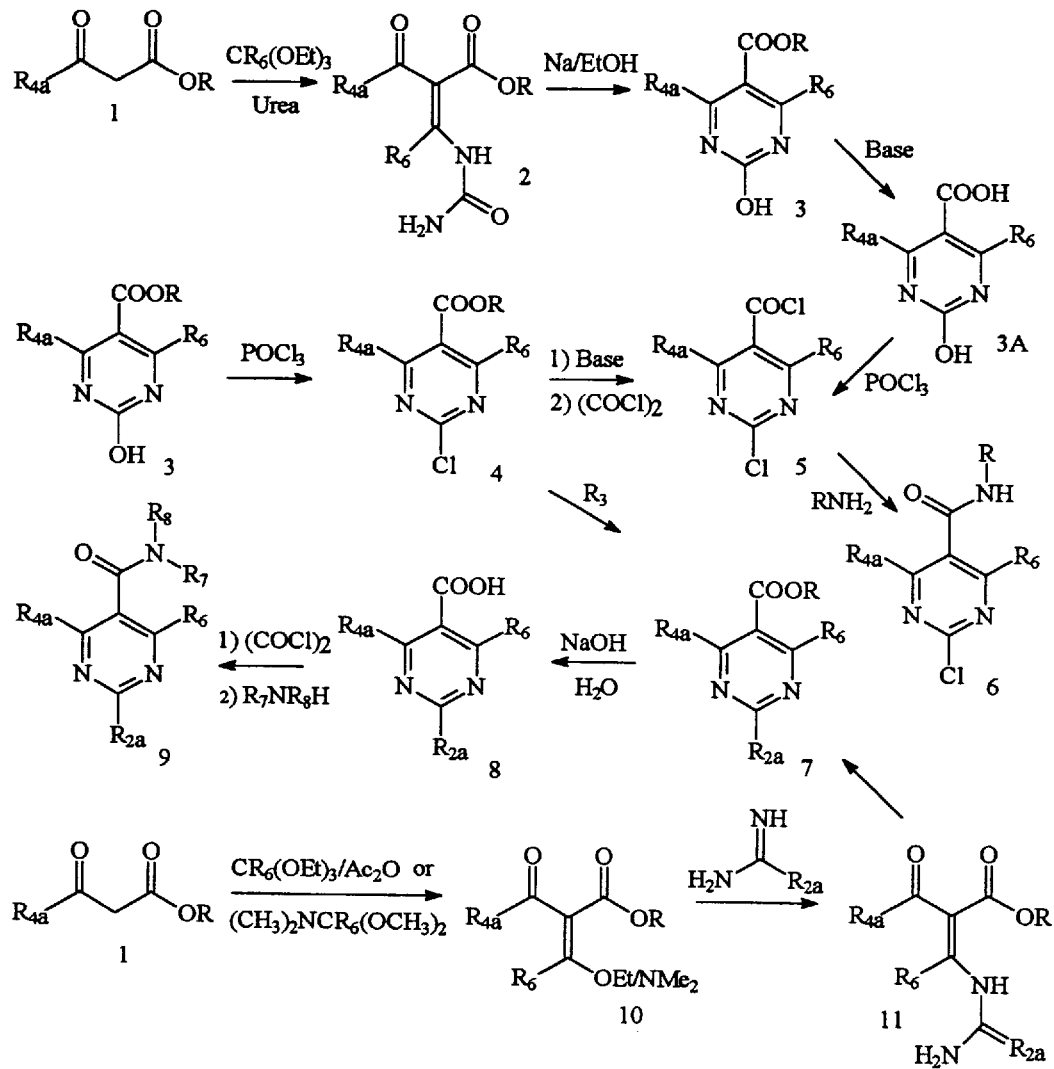
FIG. 1 illustrates a reaction scheme for the synthesis of representative pyrimidine-containing compounds of this invention.

As mentioned above, the compounds of this invention block activation of transcription factors (TFs), and thus have utility as anti-inflammatory agents in general, and in the prevention and/or treatment of a variety of conditions, including (but not limited to) immunoinflammatory and autoimmune diseases. The compounds are believed to function by inhibiting, at an early stage, transcription of deleterious proteins associated with such conditions or diseases. It is believed that this is achieved by inhibiting the kinase(s) that regulate the activation of TFs, such as NFκB and/or AP-1. By disrupting the production of these activated TFs, synthesis of pathological proteins, including proinflammatory cytokines, associated with a series of immunoinflammatory and autoimmune diseases are effectively blocked at a transcriptional level. Accordingly, the compounds of this invention have activity in both the prevention and treatment of immunoinflammatory diseases such as rheumatoid arthritis, osteoarthritis and transplant rejection (tissue and organ), as well as autoimmune diseases such as multiple sclerosis.

The compounds of this invention are generally represented by the following general structure (I):

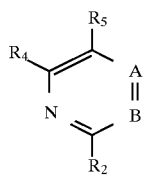

(I)

wherein A is C—$R_6$ when B is N, and A is N when B is C—$R_1$, and wherein $R_1$, $R_2$, $R_4$, $R_5$ and $R_6$ are as defined below. Thus, when A is C—$R_6$ and B is N, structure (I) is a pyrimidine-containing compound having structure (II), and when A is N and B is C—$R_1$, structure (I) is a pyrazine-containing compound having structure (III):

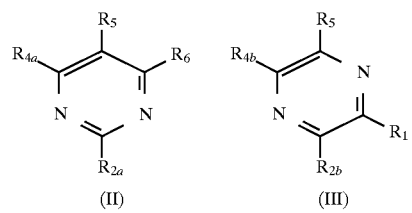

(II) (III)

In structures (I), (II) and (III) above, $R_5$ is selected from the following chemical moieties (i) through (iv):

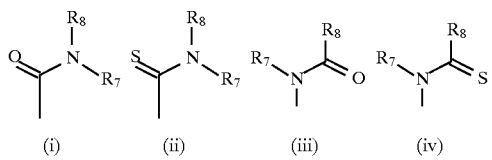

(i) (ii) (iii) (iv)

wherein $R_7$ is selected from hydrogen, —$CH_3$ and —$CH_2C_6H_5$; and $R_8$ is selected from hydrogen and an unsubstituted or substituted $C_{1-8}$alkyl, $C_{6-12}$aryl, $C_{7-12}$aralkyl, $C_{3-12}$heterocycle and a $C_{4-16}$heterocyclealkyl.

As used herein, the above terms have the following meaning:

A "$C_{1-8}$alkyl" is a straight chain or branched, cyclic or non-cyclic, saturated or unsaturated carbon chain containing from 1 to 8 carbon atoms. In one embodiment, the $C_{1-8}$alkyl is a fully saturated, straight chain alkyl selected from methyl, ethyl, n-propyl, n-butyl, n-pentyl and n-hexyl. In another embodiment, the $C_{1-8}$alkyl is a fully saturated cyclic alkyl selected from (but not limited to) cyclopropyl, cyclobutyl, cyclopentyl, cyclohexyl, methylenecyclopropyl and methylenecyclohexyl. In still a further embodiment, the $C_{1-8}$alkyl is a fully saturated, branched alkyl selected from (but not limited to) isopropyl, sec-butyl, isobutyl, tert-butyl, isopentyl and isohexyl. In yet a further embodiment, the $C_{1-8}$alkyl is an unsaturated straight chain alkyl selected from (but not limited to) ethylenyl, propylenyl, 1-butenyl, 1-pentenyl and 1-hexenyl.

A "$C_{6-12}$aryl" is an aromatic moiety containing from 6 to 12 carbon atoms. In one embodiment, the $C_{6-12}$aryl is selected from (but not limited to) phenyl, tetralinyl, and napthalenyl. In a preferred embodiment, the $C_{6-12}$aryl is phenyl.

A "$C_{7-12}$aralkyl" is an arene containing from 7 to 12 carbon atoms, and has both aliphatic and aromatic units. In one embodiment, the $C_{7-2}$aralkyl is selected from (but not limited to) benzyl, ethylbenzyl, propylbenzyl and isobutylbenzyl.

A "$C_{3-12}$heterocycle" is a compound that contains a ring made up of more than one kind of atom, and which contains 3 to 12 carbon atoms. In one embodiment, the $C_{3-12}$heterocycle is selected from (but not limited to) pyrrolyl, furanyl, thiophenyl, imidazolyl, oxazolyl, thiazolyl, pyrazolyl, pyrrolidinyl, pyridinyl, pyrimidinyl and purinyl. In a further embodiment, the $C_{3-12}$heterocycle includes the following structures:

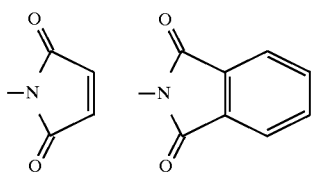

A "$C_{4-16}$heterocyclealkyl" is a compound that contains a $C_{3-12}$heterocycle linked to a $C_{1-8}$alkyl. In one embodiment, the $C_{4-16}$heterocyclealkyl is a methylene furan having the following structure:

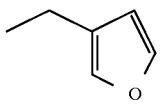

A "substituted" $C_{1-8}$alkyl, $C_{6-12}$aryl, $C_{7-12}$aralkyl, $C_{3-12}$heterocycle or $C_{4-16}$heterocyclealkyl is a $C_{1-8}$alkyl, $C_{6-12}$aryl, $C_{7-12}$aralkyl, $C_{3-12}$heterocycle or $C_{4-16}$heterocyclealkyl having one or more hydrogens replaced with a substituent selected from halogen (including —F, —Cl, —Br and —I), —OH, —R, —OR, —COOH, —COOR, —COR, —CONH$_2$, —NH$_2$, —NHR, —NRR, —SH, —SR, —SOOR, —SOOH and —SOR, where each occurrence of R is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl as defined above. In one embodiment, the substituted $C_{1-8}$alkyl is a $C_{1-8}$haloalkyl including (but not limited to) —CF$_3$ and —C$_2$F$_5$.

In structure (II) above, $R_{2a}$ is selected from halogen, an unsubstituted or substituted $C_{1-8}$alkyl, $C_{6-12}$aryl, $C_{7-12}$aralkyl, $C_{3-12}$heterocycle or $C_{4-16}$heterocyclealkyl, —CN, —OR, —NHR, —NRR and —NRNCOR, wherein each occurrence of R is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl as defined above. In one embodiment, $R_{2a}$ is selected from —Cl, —F, —CN and —CF$_3$.

In structure (III) above, $R_{2b}$ is halogen, such as —Cl or —F.

In structure (II) above, $R_{4a}$ is selected from hydrogen, halogen, an unsubstituted or substituted $C_{1-8}$alkyl, $C_{6-12}$aryl, $C_{7-12}$aralkyl, $C_{3-12}$heterocycle or $C_{4-16}$heterocyclealkyl, —CN, —OR, —NHR, —NRR and —NRNCOR, wherein each occurrence of R is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl as defined above. In one embodiment, $R_{4a}$ is selected from hydrogen, —CH$_3$, —CF$_3$, —C$_2$F$_5$, —C$_2$H$_5$, —C$_6$H$_5$ and —CH$_2$C$_6$H$_5$.

In structure (III) above, $R_{4b}$ is selected from hydrogen, halogen, —CN, and an unsubstituted or substituted $C_{1-8}$alkyl, $C_{6-12}$aryl, $C_{7-12}$aralkyl, $C_{3-12}$heterocycle or $C_{4-16}$heterocyclealkyl.

In structures (I) and (II) above, $R_6$ is selected from hydrogen, halogen, and an unsubstituted or substituted $C_{1-8}$alkyl, including (but not limited to) a $C_{1-8}$haloalkyl (such as —CF$_3$ and —C$_2$F$_5$). In one embodiment, $R_6$ is selected from hydrogen, —Cl, —F, —CH$_3$ and —CF$_3$.

In structures (I) and (III) above, $R_1$ is selected from hydrogen, —CH$_3$, —CF$_3$ and —C$_2$H$_5$.

In one embodiment, the compounds of this invention have structure (II) above, wherein $R_1$ is the chemical moiety (i). In this embodiment, the compounds disclosed herein have the following structure (IV):

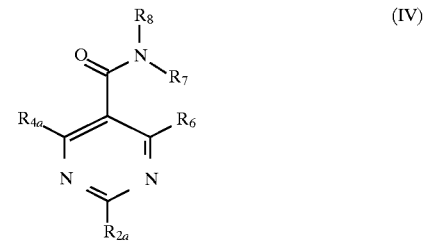

where $R_{2a}$, $R_{4a}$, $R_6$, $R_7$ and $R_8$ are as defined above. In a preferred embodiment, representative compounds of structure (IV) contain $R_{2a}$, $R_{4a}$, $R_6$, $R_7$ and $R_8$ moieties as identified in Table 1 below.

TABLE 1

| Compounds of Structure (IV) | | | | |
|---|---|---|---|---|
| $R_{2a}$ | $R_{4a}$ | $R_6$ | $R_7$ | $R_8$ |
| —Cl | —CF$_3$ | —H | —H | |
| —OCH$_3$ | —Cl | —CF$_3$ | —CH$_3$ | ⌬—X,Y,Z |
| —H | —F | —CH$_3$ | | |
| —N(CH$_3$)$_2$ | —CH$_3$ | —Cl | | |
| —CF$_3$ | —H | | | |
| —CN | —C$_2$F$_5$ | | | |
| —NHNH$_2$ | | | | ⌬—X,Y,Z |

TABLE 1-continued

Compounds of Structure (IV)

| $R_{2a}$ | $R_{4a}$ | $R_6$ | $R_7$ | $R_8$ |
|---|---|---|---|---|
| —NHPh | | | | | wherein X, Y and Z are the same or different, and independently selected from hydrogen, —OH, —R, —OR, —COOH, —COOR, —COR, —CONH$_2$, —NH$_2$, —NHR, —NRR, —SH, —SR, —SOOR, —SOOH and —SOR, where each occurrence of R is independently selected from an unsubstituted or substituted C$_{1-8}$alkyl, C$_{6-12}$aryl, C$_{7-12}$aralkyl, C$_{3-12}$heterocycle or C$_{4-16}$heterocyclealkyl.

In a preferred embodiment of the compounds disclosed in Table 1 above, X, Y and Z are the same or different, and independently selected from —H, —Cl, —F, —CF$_3$, —OH, —CH$_3$ and —OCH$_3$. In a further preferred embodiment, R$_8$ is a 3,5-bis(trifluoromethyl)phenyl moiety or a 3-trifluoromethyl-5-halo-phenyl moiety.

As mentioned above, in one embodiment of this invention the compounds have structure (II). Within one aspect of this embodiment, R$_{4a}$ is —CF$_3$ and R$_2$a is —Cl. Such compounds include (but are not limited to): 2-chloro-4-trifluoromethyl-5-N-(3',5'-bistrifluoromethylphenyl)pyrimidine carboxamide; 2-chloro-4-trifluoromethyl-5-N-(3',5'-dichlorophenyl)pyrimidine carboxamide; 2-chloro-4-trifluoromethyl-5-N-(4'-trifluoromethylphenyl)pyrimidine carboxamide; 2-chloro-4-trifluoromethyl-5-N-(phenyl)pyrimidine carboxamide; 2-chloro-4-trifluoromethyl-5-N-(cyclohexyl)pyrimidine carboxamide; 2-chloro-4-trifluoromethyl-5-N-(3',4',5'-trichlorophenyl)pyrimidine carboxamide; 2-chloro-4-trifluoromethyl-5-N-(benzyl)pyrimidine carboxamide; 2-chloro-4-trifluoromethyl-5-N-(4'-(2',1',3'-benzothiadiazole))pyrimidine carboxamide; 2-chloro-4-trifluoromethyl-5-N-(3',5'-dichloro-6'-hydroxyphenyl)pyrimidine carboxamide; 2-chloro-4-trifluoromethyl-5-N(5'-(3'-methylisoxazole))pyrimidine carboxamide; 2-chloro-4-trifluoromethyl-5-N-(3'-N-acyl-4'-fluoroaniline)pyrimidine carboxamide; 2-chloro-4-trifluoromethyl-5-N-(3-trifluoromethyl-5'-ethoxycarbonylphenyl)pyrimidine carboxamide; 2-chloro-4-trifluoromethyl-5-N-(3'-trifluoromethyl-5-(carboxamide)phenyl) pyrimidine carboxamide; 2-chloro-4-trifluoromethyl-5-N-(3',5'-dichlorophenyl)-N(methyl)pyrimidine carboxamide; and 2-chloro-4-trifluoromethyl-5-N-(3',5'-dichlorophenyl)-N-(benzyl)pyrimidine carboxamide.

Within another aspect of this embodiment, R$_{4a}$ is —CF$_3$ and R$_{2a}$ is a moiety other than —Cl. Such compounds include (but are not limited to): 2-fluoro-4-trifluoromethyl-5-N-(3',5'-bistrifluoromethyl)pyrimidine carboxamide, 5-(3',5'-bis(trifluoromethyl)phenacyl)-2-methoxy-4-trifluoromethylpyrimidine; 4-trifluoromethyl-5-N-(3',5'-dichlorophenyl)pyrimidine carboxamide; 2-dimethylamino-4-trifluoromethyl-5-N-(3',5'-dichlorophenyl)pyrimidine carboxamide; 2-triethylammonium chloride-4-trifluoromethyl-5-N-(3',5'-dichlorophenyl)pyrimidine carboxamide; 2-cyano-4-trifluoromethyl-5-N-[3',5' (bistrifluoromethyl)phenyl]pyrimidine carboxamide; 2-hydrazino-4-trifluoromethyl-5[N-(3',5'-dichlorophenyl)pyrimidine-5-carboxamide; 2-[N-(1-Aminocitraconamide)]-4-trifluoromethyl-5-[N-(3',5'-dichlorophenyl) pyrimidine-5-carboxamide; and 2-aminophenyl-4-trifluoromethyl-N-(3',5'-dichlorophenyl)pyrimidine-5-carboxamide.

Within yet a further aspect of this embodiment, R$_{2a}$ is —Cl and R$_{4a}$ is a moiety other than —CF$_3$. Such compounds include (but are not limited to): 5-N-(3',5'bis(trifluoromethyl)phenyl)-2,4-dichloro-6-methyl-pyrimidine carboxamide; 2-chloro-4-methyl-5-N-(3',5'-(bistrifluoromethyl)phenyl)pyrimidine carboxamide; 2,4-dichloro-5-N-(3',5'-bis(trifluoromethyl)benzyl)pyrimidine-5-carboxamide; and 2-chloro-4-phenyl-5-N-(3',5'-(bistrifluoromethyl)phenyl)pyrimidine carboxamide.

In another embodiment, the compounds of this invention have structure (III) above. Within one aspect of this embodiment, R$_1$ is selected from hydrogen, —CH$_3$ and —CF$_3$. Such compounds include (but are not limited to) pyrazine-containing compounds which correspond to the pyrimidine-containing compounds disclosed above. In one embodiment of structure (III), R$_{2b}$ is —Cl, R$_{4b}$ is —CF$_3$ and R$_5$ is a moiety of structure (i) above.

A small number of compounds which fall within structure (I) above have been previously disclosed and/or are commercially available. However, such compounds have not been associated with the utilities of the present invention, or possess no recognized utility. Accordingly, compounds that fall within the scope of structure (I), and which have recognized utility, are specifically excluded from the novel compounds of structure (I). However, to the extent such compounds have not been disclosed for the utilities of the present invention, they are included in the various methods of this invention.

To this end, the novel compounds of this invention do not include compounds of structure (IV) above where R$_7$ and R$_8$ are both hydrogen, and where R$_{2a}$ is selected from an unsubstituted, straight chain or branched, non-cyclic, saturated C$_{1-3}$ alkyl (i.e., —CH$_3$, —CH$_2$CH$_3$, —(CH$_2$)$_2$CH$_3$ and —CH(CH$_3$)$_2$), —N(CH$_3$)$_2$, —N(CH$_2$CH$_3$)$_2$ and —OR, where R is as defined above. Similarly, the novel compounds of structure (IV) are subject to the following provisos: (a) when R$_{2a}$ is —Cl and R$_6$ is —H, R$_{4a}$ is not —CF$_3$, —Cl, —CH$_3$ or —C(CH$_3$)$_3$, (b) when R$_{2a}$ is —Cl and both R$_{4a}$ and R$_6$ are —H, R$_8$ is not —CH(CN)C$_6$H, or —(CH$_2$)$_5$CH$_3$, and (c) when R$_2$a is —Cl and R$_{4a}$ is —Cl, R$_6$ is not —Cl or —CH$_2$Cl.

The novel compounds of this invention also do not include compounds of structure (II) when R$_5$ is moiety (iii) and (a) R$_{2a}$ is —CH$_3$, —OCH$_3$ or —N(CH$_3$)$_2$, or (b) R$_8$ is —H or —CH$_3$.

Furthermore, the novel compounds of structure (III) when R$_5$ is moiety (i) are subject to the following proviso: when R$_{2b}$ is —Cl, R$_{4b}$ and R$_1$ are not both hydrogen.

The compounds of this invention may be made by one skilled in organic synthesis by known techniques, as well as by the synthetic routes disclosed herein. For purpose of convenience, the compounds have been separated into pyrimidine-containing (structure (II)) and pyrazine-containing (structure (III)) compounds as set forth below. The pyrimidine-containing compounds of this invention may be prepared as illustrated by the reaction scheme of FIG. 1. In general, commercially available β-keto esters 1 are heated at elevated temperatures (75°–110° C.) with a mixture of urea and triethylorthoformate (or a substituted orthoformate) to provide ureido derivatives 2. Treatment of these intermediates with sodium alkoxides, such as sodium ethoxide in an alcoholic solvent at 35°–100° C., gives 2-hydroxypyrimidine esters 3 which, upon treatment with a chlorinating agent such as phosphorous oxychloride at elevated temperatures (75°–120° C.), yields 2-chloropyrimidine esters 4. The 2-hydroxypyrimidine esters 3 may also be treated with a mild base, such as lithium hydroxide, sodium hydroxide or potassium carbonate to provide the corresponding acid 3A, which may then be converted with a chlorinating agent, such as phosphorous oxychloride or thionyl chloride in an inert solvent or neat at 25°–75° C., to the acid chloride 5. Compounds of structure 6 may be prepared using standard conditions known in the art by reacting the acid chloride 5 with an amine in the presence of a base, such as potassium carbonate or dimethylaminopyridine (DMAP), in a non-protic solvent, such as methylene chloride or EtOAc at 25°–40° C., followed by standard workup.

Alternatively, pyrimidine-containing compounds of this invention may also be made by the following combinatorial procedure. Commercially available and/or readily synthesized amines, anilines and related compounds may be reacted with the acid chloride 5 in EtOAc in the presence of basic Amberlyst 21 resin. The reactions are quenched with 50 μL of water and the final products are obtained in the organic layer and concentrated. This procedure may be done in a 96 well (1 mL deep well) plate and the final products isolated as dry powders. TLC analysis is performed on each compound and indicates the purity, and GC/MS and HPLC analysis demonstrates that the desired products are synthesized (mass spectral analysis, molecular weight) and are greater than 80% pure. By this method, eighty distinct pyrimidine-containing compounds may be routinely synthesized at the same time in one 96 well plate.

In addition, compound 4 may be reacted with various nucleophiles in an aprotic solvent and at ambient temperature to provide derivatives 7. These compounds can be hydrolyzed with base to yield compounds having structure 8. Compounds of structure 8 can be converted to the acid chloride as described above, and reacted with various amines to give compounds having structure 9 using known conditions, including the combinatorial approach described above. Alternatively, compounds of structure 7 can also be prepared by reacting the β-keto ester 1 in a sequential fashion with triethylorthoformate and acetic anhydride or N,N-dimethylformamide dimethyl acetal in DMF to give intermediate 10. Reacting intermediate 10 with a variety of amidines in alcoholic solvents provides intermediate 11 which, upon addition of base, provides compounds of structure 7.

Figure 2:
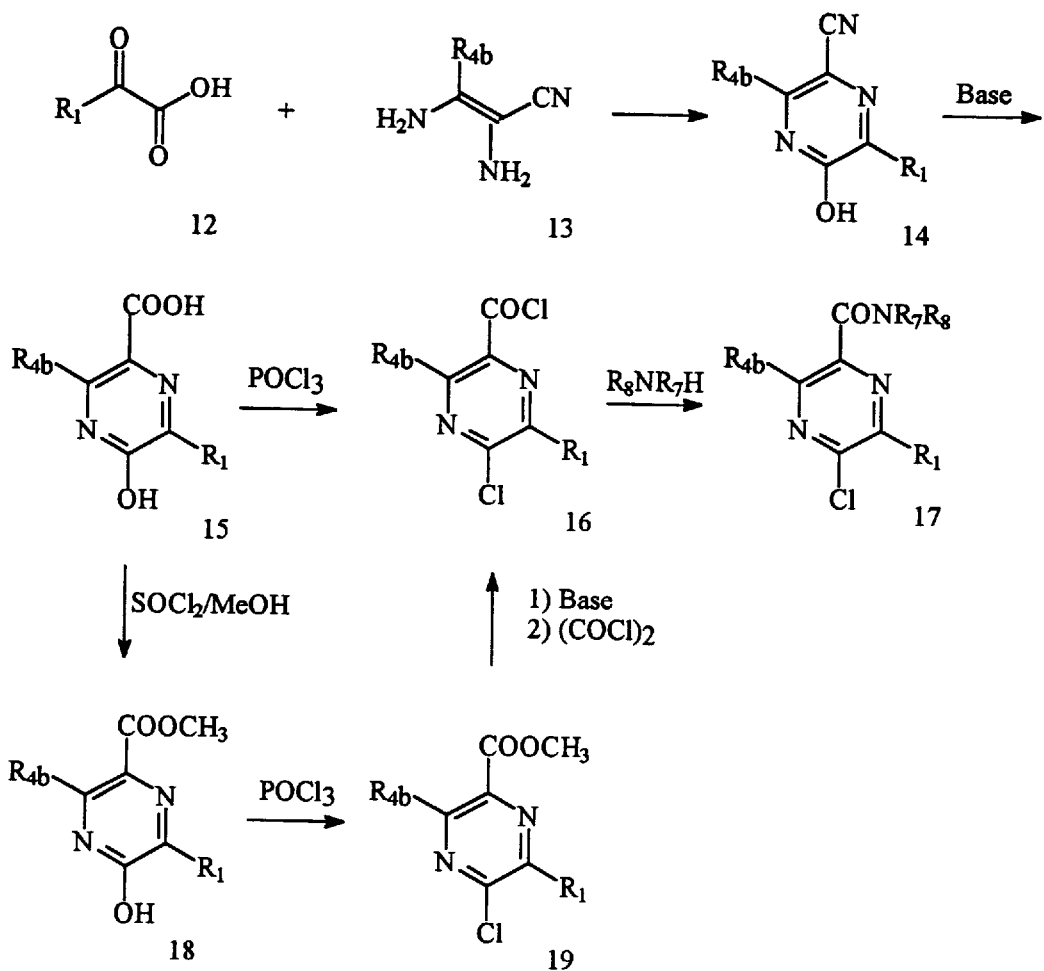
FIG. 2 illustrates a reaction scheme for the synthesis of representative pyrazine-containing compounds of this invention.

Pyrazine-containing compounds of structure (III) may be prepared as illustrated by the reaction scheme of FIG. 2. The synthesis of these compounds may begin with readily available pyruvic acid derivatives 12. These compounds are condensed with commercially available 2-cyano-1,2-diamino-2-substituted ethenes 13 in an alcoholic solvent (such as MeOH) in the presence of an acid (such as HCl) at ambient temperatures (25°–60° C.) to provide the cyano pyrazines of structure 14. The pyrazines may then be converted to the corresponding carboxylic acids 15 using a strong base such as sodium hydroxide in water, or a strong acid such as HCl, at elevated temperatures (70°–110° C.). These carboxylic acids may then be converted to 5-chloro-2-carbonyl acid chloride derivatives 16 using a chlorinating agent such as $POCl_3$ or $SOCl_2$. Treatment of 16 with various amines or anilines at ambient temperatures in an inert solvent such as EtOAc or $CH_2Cl_2$ provides compounds of structure 17.

The carboxylic acids of structure 15 can also be converted to the hydroxy ester 18 by treatment with $SOCl_2$ and MeOH at a temperature of 25°–60° C. Treatment of 18 with a chlorinating agent such as $SOCl_2$ or $POCl_3$ in the presence of DMF gives the chloro ester 19. Compound 19 can also be converted to the acid chloride 16 using a mild base such as potassium carbonate in an a protic solvent such as MeOH, followed by treatment with a chlorinating agent such as oxalyl chloride in an inert solvent such as methylene chloride at ambient temperatures.

The pyrazine-containing compounds of this invention may also be synthesized by appropriate combinatorial techniques as described. In short, commercially available and/or readily synthesized amines, anilines and related compounds may be reacted with the acid chloride 16 in EtOAc in the presence of basic Amberlyst 21 resin. The reactions are quenched with 50 μL of water and the final products are obtained in the organic layer and concentrated. This procedure may be done in a 96 well (1 mL deep well) plate and the final products isolated as dry powders. TLC analysis is performed on each compound and indicates the purity, and GC and HPLC analysis demonstrates that the desired products are synthesized (mass spectral analysis, molecular weight) and are greater than 80% pure. By this method, eighty pyrazine-containing compounds may be routinely synthesized in one 96 well plate.

Once synthesized, the compounds of this invention may be formulated for administration to a warm-blooded animal by a variety of techniques known to those skilled in the art. In one embodiment, the compound is in the form of a pharmaceutical composition for prophylactic or therapeutic use, and which contains at least one compound of this invention in combination with a pharmaceutically acceptable carrier or diluent. The compound is present in the composition in an amount which, upon administration to the animal, is effective in preventing or treating the condition of interest. Preferably, the composition includes a compound of this invention in an amount ranging from 0.01 mg to 250 mg per dosage, depending upon the route of administration, and more preferably from 1 mg to 60 mg. Appropriate concentrations, dosages and modes of administration may be readily determined by one skilled in the art.

Suitable carriers or diluents are familiar to those skilled in the formulation field. For compositions formulated as liquid solutions, acceptable carrier or diluents include saline and sterile water, and may optionally include antioxidants, buffers, bacteriostats and other common additives. The compositions of this invention may also be formulated as pills, capsules, granules or tablets which contain, in addition to the compound of this invention, diluents, dispersing and surface active agents, binders and lubricants. One skilled in the art may further formulate the compounds of this invention in any appropriate manner, and in accordance with accepted practices, such as those disclosed in *Remington's Pharmaceutical Sciences*, Gennaro, Ed., Mack Publishing Co., Easton, Pa., 1990 (incorporated herein by reference).

In another embodiment, the present invention provides methods for preventing or treating a variety of conditions. Such methods include administering a compound of this invention to a warm-blooded animal in need thereof in an amount sufficient to prevent or treat the condition. Such methods include systemic administration of a compound of this invention, preferably in the form of a composition as disclosed above. As used herein, systemic administration includes oral and parental methods of administration. For oral administration, suitable pharmaceutical compositions include powders, granules, pills, tablets and capsules, as well as liquids, syrups, suspensions and emulsions. These compositions may also include flavorants, preservatives, suspending, thickening and emulsifying agents, and other pharmaceutically acceptable additives. For parental administration, the compounds of the present invention may be prepared in aqueous injectable solutions which may contain, in addition to the compound of this invention, buffers, antioxidants, bacteriostats and other additives commonly employed in such solutions.

As mentioned above, compounds of the present invention can be used to prevent or treat a wide variety of disorders, diseases and/or illnesses. In particular, the compounds may be administered to a warm-blooded animal for prevention or treatment of rheumatoid arthritis, osteoarthritis, tissue and/or organ transplant rejection, sepsis, ARDS, asthma, trauma, oxidative stress, cell death, irradiation damage, ischemia, reperfusion, cancer, viral infection, and autoimmune diseases such as psoriasis, inflammatory bowel disease, glomerulonephritis, lupus, uveitis and chronic hepatitis.

Compounds of this invention may be screened by known and accepted techniques for their ability to function as prophylactically and/or therapeutically active agents. For example, the compounds may be evaluated in in vitro and/or in vivo assays indicative of the compound's antinflammatory and immunosuppressive properties. To this end, such compounds may first be evaluated in a number of cell-based assays which determine the ability of a compound to prevent activation of NFκB and AP-1 (see Example 56). Next, the compound's ability to attenuate cytokine levels (such as IL-2 and IL-8), which are known to be elevated in certain disease states, may be determined (see Example 57). The compounds may then be evaluated in an appropriate animal model, including rodent models of inflammation and immunosuppression (see Example 58).

It should be recognized that, for example, in the case of immunosuppressive drugs and other agents which have utility for the treatment of rheumatoid arthritis (RA), numerous studies have been performed directed to the activity of such drugs. To this end, cyclosporin A has been used in clinical trials since the late 1970's as a second-line drug and is recommended to be used only in patients with active RA. Thus, Experiment 58 was performed utilizing cyclosporin A as a positive control. A recent review of such immunosuppressive drugs, including relevant assays for the same, is presented by R. P. Carlson in *Exp. Opin. Invest. Drugs* 4(9):853–859, 1995 (incorporated herein by reference in its entirety, including cited references).

The following examples are presented for purpose of illustration, not limitation.

EXAMPLES

To summarize the examples that follow, Examples 1–54 disclose the synthesis of representative compounds of this invention, as well as intermediates thereof; Example 55 discloses the synthesis of representative compounds by combinational chemistry techniques; Examples 56–57 disclose the ability of representative compounds of this invention to inhibit NFκB, AP-1 and cytokines; and Example 58 discloses the activity of a representative compound of this invention in both graft versus host disease and contact sensitivity models.

Example 1

2-CHLORO-4-TRIFLUOROMETHYL-5-N-[3',5'-BIS(TRIFLUOROMETHYL)PHENYL]PYRIMIDINE CARBOXAMIDE

To a mixture of 3,5-bistrifluoromethylaniline (0.20 g, 0.92 mmol), Amberlyst A-21 ion exchange resin (0.02 g) in EtOAc (5 mL) was added a solution of 2-chloro-4-trifluoromethylpyrimidine-5-carbonyl chloride (0.27 g, 1.13 mmol) in EtOAc (5 mL). The mixture was stirred for 0.5 h, then quenched with water (0.20 mL). The organic layer was separated, dried over MgSO$_4$, filtered and the solvent removed under reduced pressure. The resulting oil was recrystallized from EtOH/H$_2$O to provide the title compound (0.21 g, 53% yield) as a white solid; m.p. 162°–163° C.

Example 2

2-CHLORO-4-TRIFLUOROMETHYL-5-N(4'-TRIFLUOROMETHYLPHENYL)PYRIMIDINE CARBOXAMIDE

The title compound was prepared as described in Example 1, but employing 4-trifluoromethylaniline (0.1 g, 0.41 mmol) in place of 3,5-bistrifluoromethylaniline and the acid chloride (0.10 g, 0.41 mmol), resulting in a 24% yield; m.p. 172°–173° C.

Example 3

2-CHLORO-4-TRIFLUOROMETHYL-5-N-(PHENYL)PYRIMIDINE CARBOXAMIDE

The title compound was prepared as described in Example 1, but employing aniline (0.04 g, 0.39 mmol) and the acid chloride (0.22 g, 0.90 mmol), resulting in a 62% yield; m.p. 108°–181° C.

Example 4

2-CHLORO-4-TRIFLUOROMETHYL-5-N-(CYCLOHEXYL)PYRIMIDINE CARBOXAMIDE

The title compound was prepared as described in Example 1, but employing cyclohexylamine (0.02 g, 0.18 mmol) and the acid chloride (0.05 g, 0.22 mmol), resulting in a 33% yield; m.p. 150°–151° C.

Example 5

2-CHLORO-4-TRIFLUOROMETHYL-5-N-(BENZYL)PYRIMIDINE CARBOXAMIDE

The title compound was prepared as described above in Example 1, but employing benzylamine (0.09 g, 0.92 mmol) and the acid chloride (0.25 g, 1.0 mmol), resulting in a 78% yield; m.p. 152°–153° C.

Example 6

2-CHLORO-4-TRIFLUOROMETHYL-5-N-(3',4',5'-TRICHLOROPHENYL)PYRIMIDINE CARBOXAMIDE

The title compound was prepared as described in Example 1, but employing 3,4,5-trichloroaniline (0.15 g, 0.61 mmol) and the acid chloride (0.15 g, 0.61 mmol), resulting in a 55% yield; m.p. 200°–201° C.

Example 7

2-CHLORO-4-TRIFLUOROMETHYL-5-N-(4-(2',1',3'-BENZOTHIADIAZOLE))PYRIMIDINE CARBOXAMIDE

The title compound was prepared as described above in Example 1, but employing 4-amino-2,1,3-benzothiadiazole (0.01 g, 0.07 mmol) and the acid chloride (0.025 g, 0.10 mmol), resulting in a 60% yield; m.p. 179°–180° C.

Example 8

2-CHLORO-4-TRIFLUOROMETHYL-5-N-(3',5'-DICHLORO-6'-HYDROXYPHENYL) PYRIMIDINE CARBOXAMIDE

The title compound was prepared as described in Example 1, but employing 3,5-dichloro-6-hydroxyaniline (0.02 g, 0.11 mmol) and the acid chloride (0.04 g, 0.16 mmol), and purified by chromatography ($SiO_2$, 1:1 hexanes/EtOAc) to provide the compound in a 10% yield; m.p. 211°–213° C.

Example 9

2-CHLORO-4-TRIFLUOROMETHYL-5-N-[5'-(3'-METHYLISOXAZOLE)]PYRIMIDINE CARBOXAMIDE

The title compound was prepared as described in Example 1, but employing 5-amino-3-methylisoxazole (0.02 g, 0.17 mmol) and the acid chloride (0.03 g, 0.10 mmol), resulting in a 75% yield; m.p. 170°–171° C.

Example 10

2-CHLORO-4-TRIFLUOROMETHYL-5-N-(3'-N-ACYL-4'-FLUORO-ANILINE)PYRIMIDINE CARBOXAMIDE

A solution of 2-fluoro-5-nitroaniline (1.97 g, 12.60 mmol) and a 1:1 mixture of $Ac_2O$/pyridine (20 mL) was stirred for 18 h. The resulting precipitate was filtered and washed with MeOH to provide N-acyl-2-fluoro-5-nitroaniline.

The N-acyl-2-fluoro-5-nitroaniline (0.99 g, 5.00 mmol) was dissolved in EtOH (25 mL), and then 10% Pd/C (0.12 g) was added and the solution stirred under $H_2$ for 5 h. The suspension was filtered through celite and the filtrate evaporated to dryness. The resulting oil was chromatographed ($SiO_2$, 1:3 hexanes/EtOAc) to provide 3-N-acyl-4-fluoro-aniline as a yellow oil. The aniline derivative was then coupled to 2-chloro-4-trifluoromethylpyrimidine-5-carbonyl chloride as described in Example 1 to provide the title compound in a 47% yield; m.p. 126°–127° C.

Example 11

2-CHLORO-4-TRIFLUOROMETHYL-5-N-(3'-TRIFLUOROMETHYL-5'-CARBOXAMIDEPHENYL) PYRIMIDINE CARBOXAMIDE

To a solution of 3-nitro-5-trifluoromethylbenzoic acid (1.00 g, 4.25 mmol) in $CH_2Cl_2$ (50 mL) was added oxalyl chloride (1.45 g, 13.8 mmol) followed by DMF (3 drops). An immediate evolution of gas occurred and the reaction was stirred for 18 h. The solvent was removed under reduced pressure, the resulting oil was dissolved in THF (80 mL) and cooled to 0° C. To the cold solution, $NH_4OH$ (22 mL) in THF (15 mL) was added dropwise and the mixture was stirred 18 h at room temperature. The mixture was concentrated to remove the THF and the resulting precipitate was filtered and dried. The solid was dissolved in EtOH (25 mL) and 10% Pd/C (0.12 g) was added, and the suspension was stirred 15 h under a blanket of $H_2$. The reaction was filtered through celite, and the filtrate evaporated to dryness to provide 3-carboxamide-5-trifluoromethylaniline as a yellow oil. This compound was then coupled to 2-chloro-4-trifluoromethylpyrimidine-5-carbonyl chloride as described in Example 1 to provide the title compound in a 55% yield; m.p. 218°–219° C.

Example 12

2-CHLORO-4-TRIFLUOROMETHYL-5-N-(3'-TRIFLUOROMETHYL-5'-ETHOXYCARBONYLPHENYL) PYRIMIDINE CARBOXAMIDE

To a solution of 3-nitro-5-trifluoromethylbenzoic acid (0.36 g, 1.53 mmol) in $CH_2Cl_2$ (20 mL) was added oxalyl chloride (0.58 g, 4.60 mmol) followed by DMF (3 drops). An immediate evolution of gas occurred and the reaction was stirred for 18 h. The solvent was removed under reduced pressure, the resulting oil was dissolved in THF (80 mL) and cooled to 0° C. To the cooled solution was added EtOH (5 mL) in THF (15 mL) and the mixture was stirred for 18 h at room temperature. The mixture was concentrated to remove the THF and the resulting precipitate was filtered and dried. The solid was dissolved in EtOH (25 mL) and 10% Pd/C (0.12 g) was added and the suspension was stirred for 15 h under a blanket of $H_2$. The reaction was filtered through celite and the filtrate evaporated to dryness to provide 3-ethoxycarbonyl-5-trifluoromethylaniline as a yellow oil. This compound was then coupled to 2-chloro-4-trifluoromethyl pyrimidine-5-carbonyl chloride as described above to provide the title compound in a 12% yield; m.p. 67°–71° C.

Example 13

2-CHLORO-4-TRIFLUOROMETHYL-5-N-(3',5'-DICHLOROPHENYL)-5-N-(METHYL) PYRIMIDINE CARBOXAMIDE

To a solution of 2-chloro-4-trifluoromethyl-5-N-(3,5-dichlorophenyl)pyrimidine carboxamide (0.086 g, 0.23 mmol) in DMF (20 mL) was added NaH (0.02 g, 0.53 mmol). The mixture was stirred for 0.3 h at room temperature and then MeI (0.100 mL, 1.61 mmol) was added and stirring continued for 2 h. The solution was acidified with 2N HCl and then extracted with EtOAc (3X). The combined organic layers were dried over $MgSO_4$, filtered and the solvent removed under reduced pressure. The resulting oil was chromatographed ($SiO_2$, 7:1 hexanes/EtOAc) to provide the title compound (6% yield) as a white solid; m.p. 124°–125° C.

Example 14

2-CHLORO-4-TRIFLUOROMETHYL-5-N-(3',5'-DICHLOROPHENYL)-5-N-(BENZYL) PYRIMIDINE CARBOXAMIDE

A mixture of benzaldehyde (1.04 g, 9.40 mmol), 3,5-dichloroaniline (1.71 g, 10.60 mmol), and HOAc (0.20 mL) in MeOH (35 mL) was cooled to 0° C. Then a solution of $NaBH_3CN$ (28.0 mL, 28.0 mmol, 1.0 M solution in THF) was added dropwise via a syringe pump over 0.25 h. The solution was allowed to stir an additional 0.3 h at 0° C., and then room temperature for 18 h. The excess $NaBH_3CN$ was quenched with HCl and the solvent was removed under reduced pressure. The resulting oil was dissolved in EtOAc/$H_2O$, basified with NaOH, and extracted with EtOAc. The combined organic layers were washed with brine, dried over $MgSO_4$, filtered and the solvent removed under reduced pressure. The resulting oil was purified by chromatography ($SiO_2$, 15:1 hexanes/EtOAc) to provide N-benzyl-3,5-dichloroaniline as a white solid. This compound was coupled to 2-chloro-4-trifluoromethylpyrimidine-5-carbonyl chloride as described and purified by chromatography ($SiO_2$,

Example 15

5-N-[3',5'-BIS(TRIFLUOROMETHYL)PHENYL]2, 4-DICHLORO-6-METHYLPYRIMIDINE CARBOXAMIDE

5-Carbethoxy-6-methyluracil was prepared as reported in the literature (Lamon, *J Het. Chem.*, 261, 1969); m.p. 180°–182° C. The ethyl ester was then hydrolyzed as described for 2-hydroxy-4-methylpyrimidine-5-carboxylic acid to provide 2,4-dihydroxy-6-methylpyrimidine-5-carboxylic acid in a 95% yield; m.p. >230° C.

The 2,4-dihydroxy-6-methyl pyrimidine-5-carboxylic acid was heated at reflux with $POCl_3$. The reaction mixture was concentrated and 2,4-dichloro-6-methylpyrimidine-5-carbonyl chloride was obtained by distillation (b.p. 70°–80° C., 1.5 mm/Hg). The 2,4-dichloro-6-methylpyrimidine-5-carbonyl chloride (0.15 g, 0.67 mmol) was immediately reacted with 3,5-bis(trifluoromethyl)aniline (0.15 g, 0.67 mmol) in a similar manner to that described in Example 1 to provide the title compound (0.06 g, 24%—based upon starting 2,4-dihydroxy-6-methylpyrimidine-5-carboxylic acid); m.p. 174°–176° C.

Example 16

2,4-DICHLOROPYRIMIDINE-5-CARBONYL CHLORIDE

The title compound was prepared as described in the literature (Smith and Christensen, *J. Org. Chem.* 20:829, 1955) starting from 2,4-dihydroxypyrimidine-5-carboxylic acid. The compound was obtained by distillation; b.p. 90°–100° C. (1.5 mm/Hg) in a yield of 46%; $^1$HNMR ($CDCl_3$) δ 9.29.

Example 17

ETHYL UREIDOMETHYLENE ACETOACETATE

A mixture of ethyl acetoacetate (200 g, 1.54 mol), urea (105 g, 1.54 mole) and triethyl orthoformate (228 g, 1.54 mol) was heated at 140° C. under $N_2$ for 22 h. The reaction mixture was cooled and filtered to provide the title compound in a 51% yield (156 g); m.p. 173°–174° C.

Example 18

ETHYL UREIDOMETHYLENE BENZOYLACETATE

The title compound was prepared as described in Example 17, but employing ethyl benzoylacetate (30 g, 156 mmol), resulting in a yield of 21% (12 g); m.p. 124°–126° C.

Example 19

ETHYL 2-HYDROXY-4-METHYLPYRIMIDINE-5-CARBOXYLATE

A solution of ethyl ureidomethylene acetoacetate (50 g, 250 mmol) NaOEt (22.1 g, 325 mmol) in EtOH (500 mL) was stirred at room temperature under $N_2$ for 3 days. The resulting solid was filtered and dried to yield the title compound as a sodium salt in a yield of 88% (45 g); m.p. >220° C. (dec.).

Example 20

ETHYL 2-HYDROXY-4-PHENYLPYRMIDINE-5-CARBOXYLATE

The title compound was prepared as described in Example 19, but employing ethyl ureidomethylene benzoyl acetate (12 g, 45 mmol), resulting in a yield of 15% (6 g); m.p. >260° C., (dec.).

Example 21

ETHYL 2-CHLORO-4-METHYLPYRIMIDINE-5-CARBOXYLATE

A solution of ethyl 2-hydroxy-4-methylpyrimidine-5-carboxylate (5 g, 27.5 mmol) and $POCl_3$ (84 g, 550 mmol) was heated at reflux under $N_2$ for 1 h. The reaction was cooled and concentrated. The residue was partitioned between $CHCl_3$ and $H_2O$ and the organic layer was dried ($Na_2SO_4$), filtered, and concentrated to yield the title compound in a yield of 27% (1.5 g); $^1$HNMR ($CDCl_3$) δ 9.04 (s, 1H), 4.42 (q, 2H), 2.85 (s, 3H), 1.43 (t, 3H).

Example 22

ETHYL 2-CHLORO-4-PHENYLPYRIMIDINE-5-CARBOXYLATE

The title compound was prepared as described in Example 21, but employing 2-hydroxy-4-phenylpyrimidine-5-carboxylate (6 g, 25 mmol) to give the title compound (5.5 g, 18%); m.p. 45°–47° C.

Example 23

2-CLORO-4-METHYLPYRIMIDINE-5-CARBOXYLIC ACID

A solution of ethyl 2-chloro-4-methylpyrimidine-5-carboxylate (1.0 g, 5 mmol), NaOH (0.24 g, 6 mmol) in $H_2O$ (30 mL) was stirred at room temperature for 3 h. The solution was acidified with 6N HCl and the resulting solid was filtered and dried to give the title compound (0.67 g 78%), $^1$HNMR (DMSO-$d_6$) δ 9.01 (s, 1H), 2.75 (s, 3H).

Example 24

2-CHLORO-4-PHENYLPYRIMIDINE-5-CARBOXYLIC ACID

The title compound was prepared as described in Example 23, but employing 2-chloro-4-phenylpyrimidine-5-carboxylate (4.5 g, 17 mmol), resulting in a yield of 87% (3.9 g); m.p. 105°–110° C.

Example 25

2-CHLORO-4-METHYLPYRIMIDINE-5-CARBONYL CHLORIDE

A solution of 2-chloro-4-methylpyrimidine-5-carboxylic acid (0.81 g, 4.70 mmol), oxalyl chloride (0.89 g, 7.05 mmol), DMF (2 drops) in $CH_2Cl_2$ (23 mL) was stirred at room temperature under $N_2$ for 4 h. The solution was concentrated and distilled to give the title compound (0.55 g, 61%); b.p. 90°–100° C., 1.3 mm/Hg; $^1$HNMR ($CDCl_3$) δ d 9.02 (s, 1H), 2.74 (s, 3H).

Example 26

2-CHLORO-4-PHENYLPYRIMIDINE-5-CARBONYL CHLORIDE

The compound was prepared as described above in Example 25, but employing 2-chloro-4-phenylpyrimidine- 5-carboxylic acid (3.8 g, 14 mmol), resulting in a yield of 53%; m.p. 42° C.

Example 27

2-CHLOROPYRIMIDINE-5-CARBONYLCHLORIDE

The compound was prepared as described in the literature (see, Arukwe, *J. Undheim, K Acta Chemica Scand.* B40:764, 1986).

Example 28

ETHYL ETHOXYMETHYLENE-4,4,4-TRIFLUOROACETOACETATE

A solution of 4,4,4-trifluoroacetoacetate (46 g, 0.25 mol) triethyl orthoformate (74 g, 0.50 mol) and $Ac_2O$ (77 g, 0.75 mol) was heated at 120°–140° C. for 7 h. The mixture was concentrated and distilled to give the title compound in a 98% yield (58.6 g); b.p. 80°–90° C., 1.5 mm/Hg.

Example 29

2,4-BIS(TRIFLUOROMETHYL)PYRIMIDINE-5-CARBONYL CHLORIDE

A solution of ethyl ethoxymethylene-4,4,4-trifluoroacetoacetate (15 g, 62.5 mmol) and trifluoroacetamidine (12.6 g, 112.5 mmol) in EtOH (50 mL) was heated at reflux for 24 h under $N_2$. The reaction mixture was cooled and concentrated. Chromatography ($SiO_2$, 20% EtOAc/hexane) afforded ethyl-2,4-bis (trifluoromethyl)pyrimidine-5-carboxylate as an oil (7.0 g, 39%), $^1$HNMR ($CDCl_3$) δ 9.37 (s, 1H), 3.70 (q, 2H), 1.27 (t, 3H).

A solution of ethyl-2,4-bis(trifluoromethyl)pyrimidine-5-carboxylate (5.0 g, 17 mmol) and NaOH (0.72 g, 18 mmol) in EtOH (20 mL) and $H_2O$ (50 mL) was stirred at room temperature for 1 h. The solution was acidified (HCl) and the resulting solid was filtered and dried to give 2,4-bis (trifluoromethyl)-pyrimidine-5-carboxylic acid (1.5 g, 25%), m.p. 59° C., $^1$HNMR (DMSO-$d_6$) δ 9.62 (s, 1H).

The desired acid chloride was obtained from 2,4-bis (trifluoromethyl)pyrimidine-5-carboxylic acid in a manner similar to that described in Example 25 in a yield of 44%; b.p. 105° C. (1.5 mm/Hg); $^1$HNMR ($CDCl_3$) δ 9.12 (s, 1H).

Example 30

2-CHLORO-4-TRIFLUOROMETHYLPYRIMIDINE-5-CARBOXYLIC ACID

A solution of 2-chloro-4-trifluoromethylpyrimidine-5-carbonyl chloride (2.1 g, 8.6 mmol) in $H_2O$ (10 mL) was stirred at 0° C. under $N_2$ for 0.5 h. The resulting solid was filtered and dried to give the title compound (1.91 g, 98% yield); m.p. 232°–234° C. (dec.).

Example 31

2-CYANO-4-TRIFLUOROMETHYLPYRIMIDINE-5-CARBONYLCHLORIDE

To a solution of 2-chloro-4-trifluoromethylpyrimidine-5-carboxylic acid (2.80 g, 12.4 mmol) in THF (50 mL) at 0° C. was added $Me_3N$ (bubbled for 5 minutes). The reaction was kept at 0° C. for 0.25 h and the resulting solid was filtered to provide 2-trimethylammonium chloride-4-trifluoromethylpyrimidine-5-carboxylic acid (3.40 g, 97% yield); m.p. 120°–121° C. (dec.).

A solution of 2-trimethylammonium chloride-4-trifluoromethylpyrimidine-5-carboxylic acid (3.62 g, 12.7 mmol) and KCN (0.99 g, 15.2 mmol) in DMF (36.5 mL) and $H_2O$ (18.3 mL) was stirred at room temperature under $N_2$ for 0.25 h. The reaction mixture was concentrated and dissolved in EtOAc (400 mL). The EtOAc layer was washed with $H_2O$ (4×100 mL), brine (100 mL) and dried ($Na_2SO_4$). The EtOAc layer was filtered and concentrated to yield 2-cyano-4-trifluoromethylpyrimidine-5-carboxylic acid (2.03 g, 74% yield); m.p. 148°–149° C. (dec.).

A solution of 2-cyano-4-trifluoromethylpyrimidine-5-carboxylic acid (2.0 g, 9.2 mmol), oxalyl chloride (1.4 g, 11 mmol) and DMF (4 drops) in $CH_2Cl_2$ (46 mL) was stirred at room temperature under $N_2$ for 0.75 h. The reaction was concentrated and distilled (b.p. 100° C., 1.5 mm/Hg) to give the title compound (1.8 g, 82% yield); $^1$HNMR ($CDCl_3$) δ 9.49 (s, 1H).

Example 32

2-PHENYLPYRIMIDINE-5-CARBONYL CHLORIDE

A solution of ethyl 3-N,N-dimethylamino-2-formylacrylate (4.0 g, 23 mmol) (Arnold, *Coll. Czech. Chem. Commun.* 26:3051, 1961), benzamidine hydrochloride (4.0 g, 26 mmol) and sodium (0.65 g, 28 mmol) in EtOH (40 mL) was heated at reflux for 1 h. The solution was filtered and concentrated and the residue partitioned between EtOAc and dilute HCl (10%). The organic layer was dried ($Na_2SO_4$), and concentrated to give ethyl 2-phenylpyrimidine-5-carboxylate (4.0 g, 75% yield); m.p. >220° C. (dec.).

The corresponding 2-phenylpyrimidine-5-carboxylic acid was prepared in a yield of 80% (0.35 g) starting from ethyl 2-phenylpyrimidine-5-carboxylate in a similar manner to that described in Example 23; m.p. >220° C. (dec.).

The title compound was prepared in a quantitative yield from 2-phenylpyrimidine-5-carboxylic acid in a similar manner to that described in Example 25; m.p. 135° C.

Example 33

ETHYL 2-TRIFLUOROMETHYL-4-HYDROXYPYRIMIDINE-5-CARBOXYLATE

A solution of diethyl ethoxymethylenemalonate (35.0 g, 162 mmol), trifluoroacetamidine (18 g, 162 mmol) and NaOEt (11.0 g, 162 mmol) in EtOH (200 mL) was heated at reflux for 6 h. The reaction mixture was concentrated and $H_2O$ (48 mL) was added. The resulting solid was filtered, washed with $Et_2O$ (300 mL) and $H_2O$ (200 mL), and dried to give the title compound (21 g, 50% yield); m.p. >220° C. (dec.); $^1$HNMR (DMSO-$d_6$) δ 8.38, 4.16 (q, 2H), 1.25 (q, 3H).

Example 34

2-TRIFLUOROMETHYL-4-CHLOROPYRIMIDINE-5-CARBONYL CHLORIDE

A solution of ethyl 2-trifluoromethyl-4-hydroxypyrimidine-5-carboxylate (5.00 g, 19.4 mmol) and NaOH (0.93 g, 23.3 mmol) in $H_2O$ (20 mL) was stirred at 60° C. for 15 h. The reaction was acidified (conc. HCl) and concentrated until a solid began to form. The solid was filtered and dried to give 2-trifluoromethyl-4-hydroxypyrimidine-5-carboxylic acid (2.1 g, 53% yield); $^1$HNMR (DMSO-d$_6$) δ 8.83 (s, 1H).

A solution of 2-trifluoromethyl-4-hydroxypyrimidine-5-carboxylic acid (2.0 g, 10.4 mmol), POCl$_3$ (32 g, 212 mmol) and SOCl$_2$ (25 g, 212 mmol) was heated at reflux for 4 days. The reaction was concentrated and distilled (b.p. 90°–95° C., 1.5 mm/Hg) to provide the title compound (2.1 g, 81% yield), $^1$HNMR (CDCl$_3$) δ 9.45 (s, 1H).

Example 35

2-CHLORO-4-PENTAFLUOROETHYLPYRIMIDINE-5-CARBONYL CHLORIDE

A solution of ethyl 2-hydroxy-4-pentafluoroethylpyrimidine-5-carboxylate (4.0 g, 13 mmol) and NaOH (1.60 g, 39 mmol) in EtOH (20 mL) and H$_2$O (45 mL) was heated at reflux for 1 h. The solution was cooled and acidified (conc. HCl). The resulting solid was filtered and dried to provide 2-hydroxy-4-pentafluoroethylpyrimidine-5-carboxylic acid (3.3 g, 98% yield); $^1$H-NMR (DMSO-d$_6$) δ 9.90 (bs, 1H), 8.43 (s, 1H).

A solution of 2-hydroxy-4-pentafluoroethylpyrimidine-5-carboxylic acid (3.33 g, 12.9 mmol) in SOCl$_2$ (27.7 g, 233 mmol) was heated at reflux for 0.5 h. Then POCl$_3$ (35.6 g, 233 mmol) was added to the reaction mixture and heating continued for 36 h. The reaction mixture was concentrated and distilled (b.p. 80°–85° C., 1 mm/Hg) to give the title compound (1.2 g, 35% yield). $^1$H NMR (DMSO-d$_6$) δ 9.18 (s, 1H).

Example 36

4-TRIFLUOROMETHYL-5-N(3',5'-DICHLOROPHENYL)PYRIMIDINE CARBOXAMIDE

A solution of 2-chloro-4-trifluoromethyl-5-N-(3,5-dichlorophenyl)pyrimidine carboxamide (0.10 g, 0.27 mmol), Mg$_2$O (0.024 g, 0.59 mmol) and 5% Pd/C (0.01 g) in EtOH (1.8 mL) and water (0.9 mL) was stirred at room temperature under a blanket of H$_2$ for 2.5 h. The reaction mixture was concentrated and chromatographed (SiO$_2$, 9% EtOAc/hexane) to yield the title compound (0.05 g, 53% yield); m.p. 189°–190° C.

Example 37

2-DIMETHYLAMINO-4-TRIFLUOROMETHYL-5-N-(3',5'-DICHLOROPHENYL) PYRIMIDINE CARBOXAMIDE

A solution of 2-chloro-4-trifluoromethyl-5-N-(3,5-dichlorophenyl)pyrimidine carboxamide (0.13 g, 0.36 mmol) and dimethyl amine (0.10 g, 2.20 mmol) in MeOH was stirred at room temperature for 3 h. The reaction mixture was concentrated and chromatographed (SiO,, 5% EtOAc/hexane) to afford the title compound (0.022 g, 16% yield); m.p. 163°–164° C.

Example 38

2-TRIETHYLAMMONIUM CHLORIDE-4-TRIFLUOROMETHYL-5-N-(3',5'-DICHLOROPHENYL) PYRIMIDINE CARBOXAMIDE

A solution of 2-chloro-4-trifluoromethyl-5-N-(3',5'-dichlorophenyl)pyrimidine carboxamide (0.10 g, 0.27 mmol) and triethylamine (0.027 g, 0.27 mmol) in dry THF was stirred for 24 h. The solid was filtered, washed with Et$_2$O, and dried to afford the title compound (0.031 g, 24% yield); m.p. 158°–159° C.

Example 39

2-CHLORO-4-METHYL-5-N-[3',5'-BIS(TRIFLUOROMETHYL)PHENYL]PYRIMIDINE CARBOXAMIDE

A solution of 2-chloro-4-methylpyrimidine-5-carbonyl chloride (0.10 g, 0.53 mmol), 3,5-bis(trifluoromethyl)aniline (0.12 g, 0.53 mmol) and Amberlyst A-21 resin (0.0 g) in EtOAc (5.3 mL) was stirred at room temperature for 1 h. The solution was filtered, concentrated and chromatographed (SiO$_2$, 10% EtOAc/hexane) to afford the title compound (0.17 g, 84% yield); m.p. 156°–157° C.

Example 40

2,4-DICHLORO-5-N-[3',5'-BIS(TRIFLUOROMETHYL)BENZYL]PYRIMIDINE-5-CARBOXAMIDE

The title compound was prepared as described in Example 1, but employing 2,4-dichloropyrimidine-5-carbonylchloride (0.10 g, 0.40 mmol) and 3,5-bistrifluoromethylbenzylamine (0.10 g, 0.45 mmol) to give the compound in a 61% yield (0.12 g); m.p. 144°–145° C.

Example 41

2,4-DICHLORO-5-N-[3',5'-BIS(TRIFLUOROMETHYL)PHENYL]PYRIMIDINE-5-CARBOXAMIDE

The title compound was prepared as described in Example 1, but employing 2,4-dichloropyrimidine-5-carbonyl chloride to give the compound in a 97% yield (0.28 g); m.p. 104°–105° C.

Example 42

2-CYANO-4-TRIFLUOROMETHYL-5-N-[3',5'-BIS(TRIFLUOROMETHYL)PHENYL]PYRIMIDINE CARBOXAMIDE

The title compound was prepared as described in Example 1, but employing 2-cyano-4-trifluoromethylpyrimidine-5-carbonyl chloride (0.11 g, 0.46 mmol) to give the compound in a 96% yield (0.19 g); m.p. 146°–147° C.

Example 43

2-CHLORO-4-PHENYL-5-N-[3',5'-BIS(TRIFLUOROMETHYL)PHENYL]PYRIMIDINE CARBOXAMIDE

A solution of 2-chloro-4-phenylpyrimidine-5-carbonyl chloride (0.10 g, 0.40 mmol), 3,5-bis(trifluoromethyl) aniline (0.08 g, 0.40 mmol) and Et$_3$N (0.04 g, 0.40 mmol) in EtOAc was stirred at room temperature for 2 h. The solution was concentrated and chromatographed (SiO$_2$, 5% EtOH/CHCl$_3$) to afford the title compound (0.08 g, 45% yield); m.p. 154° C.

Example 44

2-HYDRAZINO-4-TRIFLUOROMETHYL-5-N(3',5'-DICHLOROPHENYL)PYRIMIDINE-5-CARBOXAMIDE

A solution of 2-chloro-4-trifluoromethyl-5-N-(3',5'-dichlorophenyl)pyrimidine carboxamide (0.10 g, 0.27 mmol) and hydrazine (0.009 g, 0.54 mmol) in THF was stirred under $N_2$ at room temperature for 14 h. The solution was filtered, concentrated and chromatographed ($SiO_2$, 20% EtOAc/hexane) to afford the title compound (0.08 g, 79% yield), $^1$HNMR (acetone-$d_6$) δ 10.08 (bs, 1H), 9.64 (bs, 1H), 8.89 (s, 1H), 7.80 (s, 2H), 7.24 (s, 1H), 2.79 (bs, 2H).

Example 45

2-[N-(1-AMINOCITRACONAMIDE)]-4-TRIFLUOROMETHYL-5-[N-(3',5'-DICHLOROPHENYL)]-PYRIMIDINE-5-CARBOXAMIDE

A solution of 2-hydrazino-4-trifluoromethyl-5-[N-(3',5'-dichlorophenyl)pyrimidine carboxamide (0.08 g, 0.21 mmol) and citraconic anhydride (0.024 g, 0.21 mmol) in $CHCl_3$ (2.1 mL) was heated at reflux under $N_2$ for 24 h. The solution was concentrated and chromatographed ($SiO_2$, 33% EtOAc/hexane) to afford the title compound (0.06 g, 62% yield); m.p. 182°–183° C.

Example 46

2-PHENYLAMINO-4-TRIFLUOROMETHYL-5-N-(3',5'-DICHLOROPHENYL)-PYRIMIDINE-5-CARBOXAMIDE

A solution of 2-chloro-4-trifluoromethyl-5-N-(3',5'-dichlorophenyl)pyrimidine carboxamide (0.10 g, 0.27 mmol) and aniline (0.06 g, 0.59 mmol) in dry THF (2.7 mL) was stirred at room temperature under $N_2$ for 18 h. The reaction mixture was filtered, concentrated and chromatographed ($SiO_2$, 50% $CHCl_3$/hexane) to afford the title compound (0.10 g, 91% yield); m.p. 228°–229° C.

Example 47

METHYL 5-CHLORO-6-METHYL-2-PYRAZINE CARBOXYLATE

To a solution of methyl 4,5-dihydro-6-methyl-5-oxo-2-pyrazine carboxylate (M. Mano, T. Seo, K. Imai, Chem. Pharm. Bull 10:3057–3063, 1980) in DMF (20 mL) was added $POCl_3$ (20 mL). The reaction was refluxed for 0.5 h and then poured into ice. The aqueous layer was extracted with $CHCl_3$ dried ($MgSO_4$) and concentrated. The residue was chromatographed ($SiO_2$, $CHCl_3$) to provide the title compound (2.34 g, 52% yield); m.p. 49°–50° C.

Example 48

5-CHLORO-6-METHYL-2-PYRAZINECARBOXYLIC ACID

A mixture of methyl 5-chloro-6-methyl-2-pyrazine carboxylate (0.16 g, 0.86 mmol), $K_2CO_3$ (0.31 g, 2.18 mmol) and $H_2O$ was stirred for 2 h at room temperature. The reaction was filtered and acidified (20% HCl), and the resulting solid collected to provide the title compound (0.057 g, 39% yield); m.p. 116°–117° C.

Example 49

2-CHLORO-5-N-(BISTRIFLUOROMETHYL ANILINE) PYRAZINE CARBOXAMIDE

The title compound was prepared in a yield of 51% (0.08 g) using the same procedure as outlined in Example 1, except substituting 2-chloro-5-pyrazine carbonyl chloride (0.1 g, 0.57 mmol.) in place of the pyrimidine carbonyl chloride; m.p. 101°–102° C.

Example 50

2-TRIMETHYLAMMONIUM CHLORIDE-4-TRIFLUOROMETHYL-5-PYRIMIDINE CARBOXYLIC ACID

A solution of 2-chloro-4-trifluoromethylpyrimidine-5-carboxylic acid (6.0 g, 27 mmol) and excess trimethyl amine in THF (60 mL) was stirred for 5 min. The solid was filtered and dried to yield 97% (7.1 g) of the title compound; $^1$H NMR (DMSO-$d_6$) δ 9.19 (s, 1H), 2.72 (s, 9H).

Example 51

2-FLUORO-4-TRIFLUOROMETHYL-5-PYRIMIDINE CARBOXYLIC ACID

A mixture of 2-trimethylammonium chloride-4-trifluoromethyl-5-pyrimidine carboxylic acid (4.3 g, 15 mmol), KF (1.8 g, 30 mmol), DMF (40 mL) and $H_2O$ (20 mL) was stirred for 0.5 h. The mixture was concentrated, acidified and extracted with $Et_2O$. The $Et_2O$ layer was concentrated to yield 47% (1.6 g) of the title compound; $^1$H NMR (DMSO-$d_6$) δ 9.41 (s, 1H).

Example 52

2-FLUORO-4-TRIFLUOROMETHYL-5-PYRIMIDINE CARBONYL CHLORIDE

The title compound was prepared as described in Example 25, but employing a solution of 2-fluoro-4-trifluoromethylpyrimidine-5-carboxylic acid (1.5 g, 7.1 mmol) and oxalyl chloride (1.0 g, 8 mmol), DMF (2 drops) in $CH_2Cl_2$ (30 mL) resulted in a 75% yield (1.2 g); $^1$H NMR ($CDCl_3$) δ 9.42 (s, 1H).

Example 53

2-FLUORO-4-TRIFLUOROMETHYL-5-N-[3',5'-BIS(TRIFLUOROMETHYL)PHENYL] PYRIMIDINE CARBOXAMIDE

The title compound was prepared as described in Example 1, but employing a solution of 2-fluoro-4-trifluoromethylpyrimidine-5-carbonyl chloride (0.05 g, 0.22 mmol) and 3,5-bis(trifluoromethyl)aniline (45 mg, 0.2 mmol) in EtOAc (2 mL) resulted in a 22% yield (0.02 g); m.p. 133°–135° C.

Example 54

2-CHLORO-4-TRIFLUOROMETHYL-5-PYRIMIDINE CARBONYL CHLORIDE

The title compound was prepared as described in Example 25, but employing a solution of 2-chloro-4-trifluoromethylpyrimidine-5-carboxylic acid (1.5 g, 7.1 mmol) and oxalyl chloride (1.0 g, 8 mmol) in $CH_2Cl_2$ (30 mL) resulted in a 70% yield (1.1 g); $^1$H NMR ($CDCl_3$) δ 9.31 (s, 1H).

Example 55

SYNTHESIS OF REPRESENTATIVE COMPOUNDS BY COMBINATORIAL CHEMISTRY TECHNIQUES

This example illustrates the synthesis of a representative class of compounds of this invention by combinatorial chemistry. It should be understood that, while a specific class of compounds are illustrated in this example, the following procedure may be employed to synthesize other compounds of this invention.

Into wells 2–11 of a 96 well 1 ml plate (rows 1 and 12 left open as controls) was added 5 mg of Amberlyst 21 resin, 0.2 ml of EtOAc and 22.4 μmol of 80 different amine derivatives. Then to each well was added 25.0 μmol of the appropriate 5-carbonyl chloride (for example 2-chloro-4-trifluoromethylpyrimidine-5-carbonyl chloride). The 96 well plate was sonicated for 0.3 h and 50 μL of $H_2O$ was added to each well. The plate was sonicated for an additional 0.25 h, and the EtOAc layer from each well was removed and concentrated to provide 80 individual compounds. Thin-layer chromatography, HPLC and GC/MS analysis indicated that the desired compounds had been produced at >90% purity. This approach can be used to generate large numbers of derivatives for each substituted pyrimidine prepared, and can be used to routinely prepare >160 derivatives for each of the different 5-carbonyl pyrimidines.

Example 56

INHIBITION OF THE ACTIVATION OF NFκB AND AP-1

A. NFκB ASSAY

Stable human Jurkat T-cells containing an NFκB binding site (from the MHC promoter) fused to a minimal SV-40 promoter driving luciferase expression were used in this experiment. Cells were split to $3 \times 10^5$ cells/mL every 2–3 days (cell concentration should not exceed $1 \times 10^6$ cells/mL to keep the cells proliferating in log phase). These cells were counted, resuspended in fresh medium containing 10% Serum-Plus at a density of $1 \times 10^6$ cells/mL and plated in 96 well round bottom plates (200 μL per well) 18 hours prior to starting the experiment.

Compounds of this invention, dissolved in dimethyl sulfoxide (3.3, 0.33 and 0.03 μg/mL), were then added to the 96 well plates containing the cells and the plates are incubated for 0.5 h at 37° C. Then 50 ng/mL of phorbol 12-myristate-13-acetate (PMA) and 1 μg/mL of phytohemagglutinin (PHA) was added to each well and the cells were incubated for an additional 5 h at 37° C. The plates were centrifuged at 2200 RPM for 3 minutes at room temperature and then the medium was removed. To each well was added 60 μL of cell lysis buffer and the plates were left at room temperature for 0.25 h. Then 40 μL of each cell extract was transferred to a black 96 well plate and 50 μL of luciferase substrate buffer was added. Luminescence was immediately measured using a Packard TopCount.

B. AP-1 ASSAY

For AP-1, the assay was run as described above for NFκB except stable Jurkat T-cells were used that contained a the −73 collagenase promoter driving luciferase expression. In addition, the concentration of PMA used was 5 ng/mL.

C. RESULTS

Figure 3:
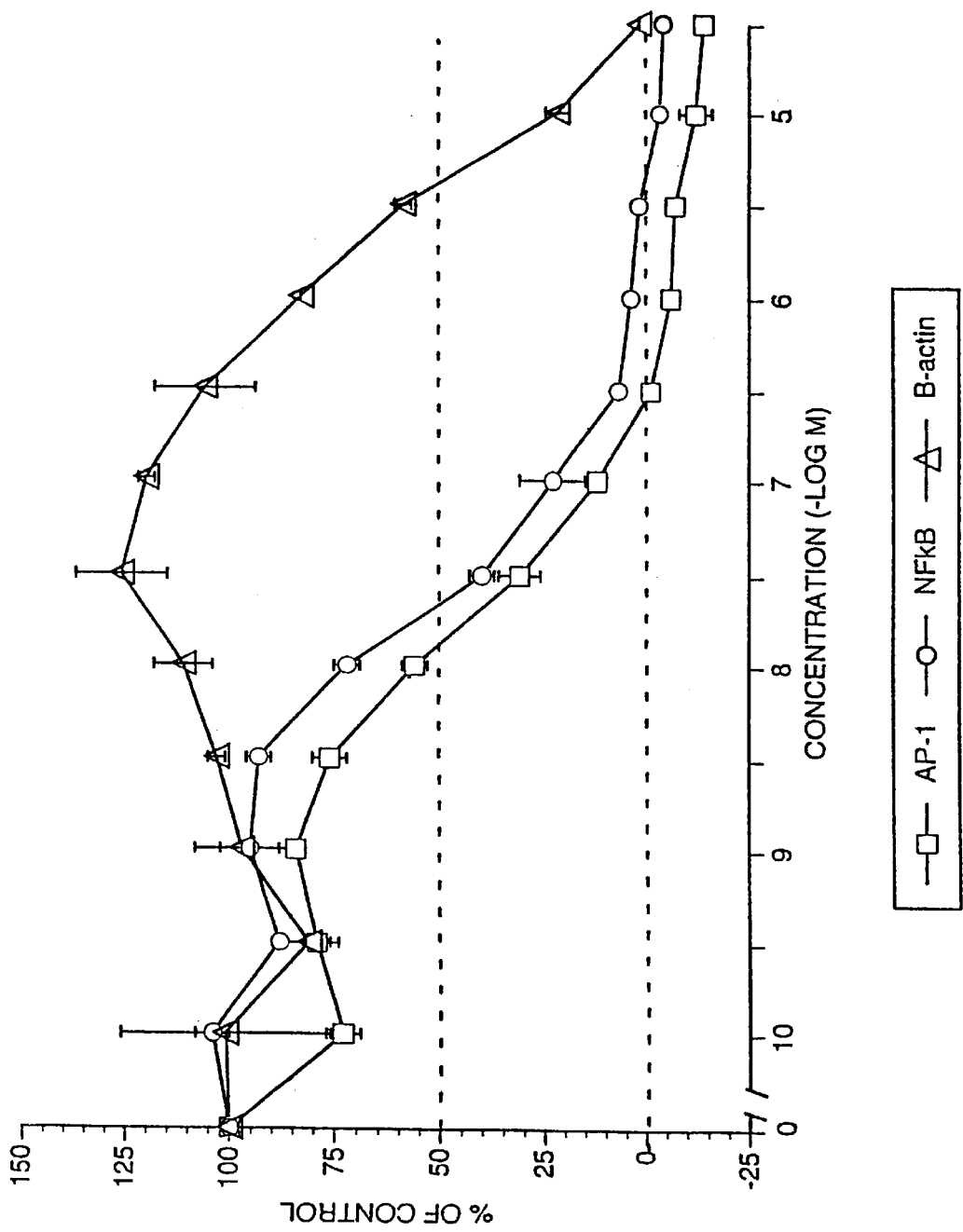
FIG. 3 illustrates the ability of a representative compound of this invention to inhibit the activation of NFκB and AP-1.

The results of the above assays for a representative compound of this invention, 2-chloro-4-trifluoromethyl-5-N-(3',5'-bistrifluoromethylphenyl)pyrimidine carboxamide, as percent inhibition versus control are presented in FIG. 3. This figure also indicates activity of β-actin which was employed in these assays as a control cell line indicating effects on transcription. The lack of β-actin activity evidences selectivity of the test compounds for the transcription factors AP-1 and NFκB.

Expressed as $IC_{50}$'s, the results of these assays on additional test compounds are summarized in Table 2 below.

TABLE 2

| Test Compound (Example #) | NFκ/AP-1 $IC_{50}$ (μM) |
| --- | --- |
| 1 | 0.03 |
| 2 | 0.75 |
| 6 | 0.8 |
| 8 | 6.0 |
| 10 | 1.0 |
| 11 | 5.0 |
| 12 | 0.4 |
| 13 | 5.0 |
| 15 | 0.8 |
| 39 | 0.075 |
| 41 | 0.6 |
| 42 | >10 |
| 43 | 0.5 |
| 45 | 2.0 |

Based on the results of this experiment, representative compounds of this invention were found to be effective at inhibiting the activation of transcription factors (i.e., NFκB and AP-1) involved in gene transcription, and therefore have utility as, for example, immunosuppressive agents.

Example 57

INHIBITION OF CYTOKINES

Figure 4:
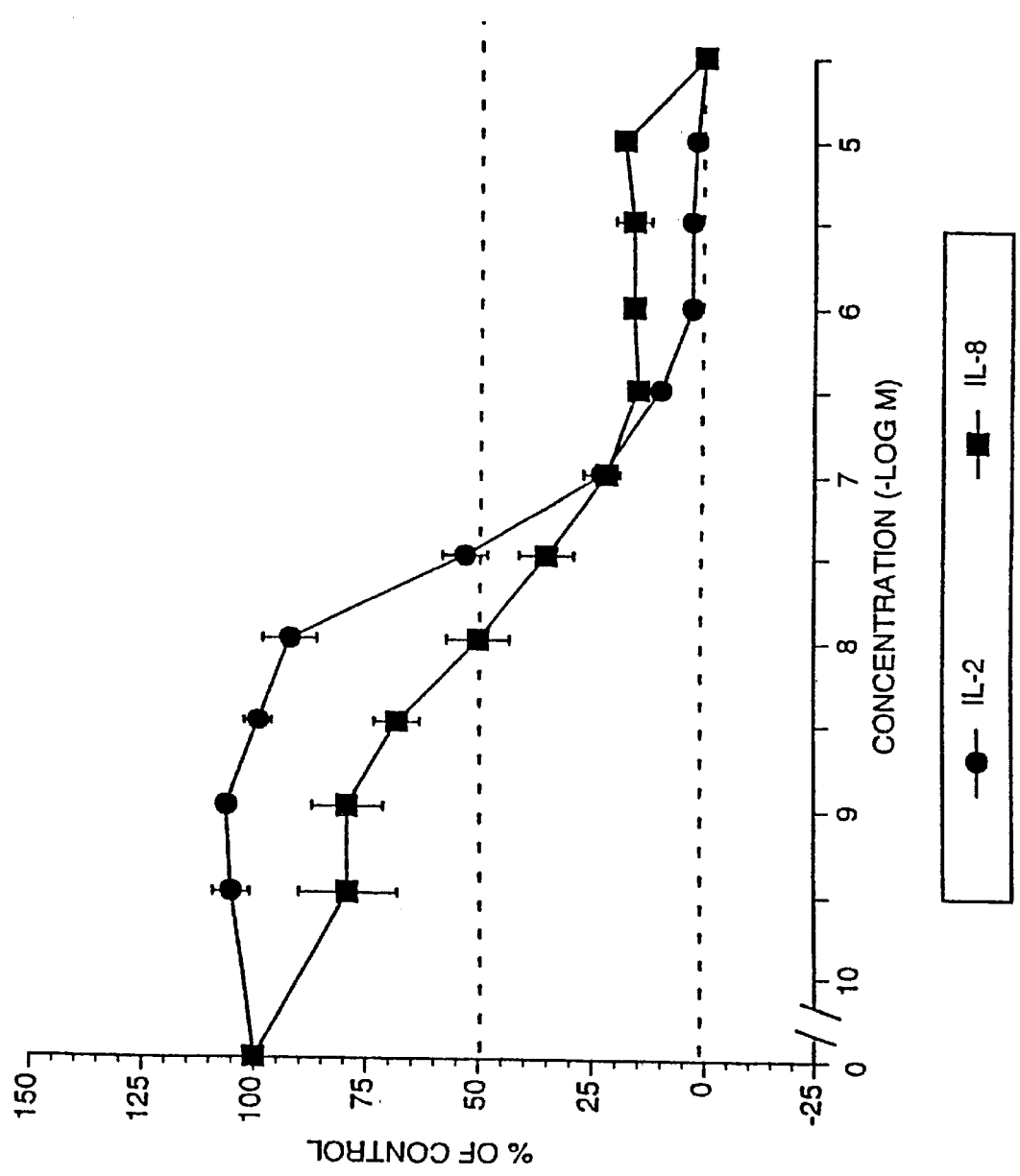
FIG. 4 illustrates the ability of a representative compound of this invention to inhibit IL-2 and IL-8.

To determine the effects of compounds on PMA/PHA-induced cytokine production, supernatants from either the NFκB (for IL-8) and AP-1 (for IL-2) reporter gene assays of Example 56 were collected and saved. Cytokine levels in the supernatants (25–50 μL aliquots) were determined by ELISA. The results of this experiment for a respresentative compound of this invention, 2-chloro-4-trifluoromethylhylphenlyl)pyrimidine carboxamide, is presented in FIG. 4 (expressed as percent inhibition versus control).

Example 58

IN VIVO ACTIVITY OF REPRESENTATIVE COMPOUND

The murine popliteal lymph node (PLN) assay is a graft vs. host model that predicts activity of compounds in blocking human transplant rejection. The delayed-type hypersensitivity response to oxazolone is a standard contact sensitivity model. Both of these models are used routinely to evaluate compounds that are used clinically. For example, cyclosporin and cyclophosphamide are active in these models and are used clinically (Morris et al., *Transplantation Proceedings* 22(Suppl. 1):110–112, 1990).

A. POPLITEAL LYMPH NODE MODEL

Spleens were removed from donor BALB/c mice and splenocytes were isolated then irradiated (3,000 rads) to prevent donor cell proliferation. After washing and adjusting cell density, $2.5 \times 10^6$ cells were injected subcutaneously into the left hind footpad of C3H mice. On day 4, the mice were sacrificed and left popliteal lymph nodes (PLNs) were weighed.

The compound of Example 1, 2-chloro-4-trifluoromethyl-5-N-(3',5'-bistrifluoromethylphenyl)pyrimidine carboxamide, was administered once daily by intraperitoneal injection beginning one day before footpad injection (day 0) through day 4. The compound was suspended, immediately prior to use, at a concentration of 5 mg/mL in 0.25% methyl cellulose (Sigma) using a glass-teflon homogenizer. For doses of 10, 20 and 30 mg/kg, appropriate dilutions of the stock solution were made so that 0.1 mL/10 g body weight was administered by intraperitoneal injection.

Figure 5:
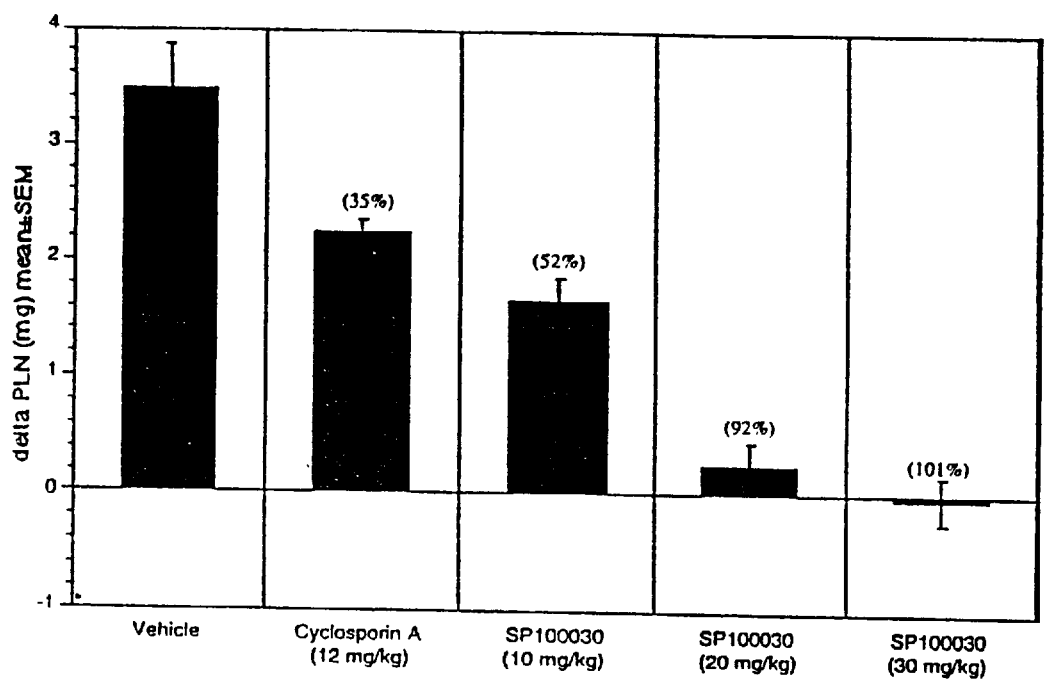
FIG. 5 illustrates the ability of a representative compound of this invention to cause a dose-dependent suppression of alloantigen-induced PLN proliferation.

The results of this experiment, presented in FIG. 5, demonstrate that a representative compound of this invention caused a dose-dependent suppression of alloantigen-induced PLN proliferation. The lowest dose of this compound, 10 mg/kg, caused a 52% inhibition of proliferation whereas cyclosporin A, at 12 mg/kg, caused a 35% inhibition.

B. DELAYED TYPE HYPERSENSITIVITY STUDY

On day 0, oxazolone (100 μL of a 3% solution) was applied to the shaved abdomen of mice. On day 7, a challenge application of oxazolone was applied (10 μL) around the right ear. The compound of Example 1, 2-chloro-4-trifluoromethyl-5-N-(3,5-bistrifluoromethylphenyl) pyrimidine carboxamide, was administered from days –2 to 7 by intraperitoneal injection. It was prepared immediately prior to use by suspending it in 0.25% methyl cellulose (Sigma) using a glass-teflon homogenizer. For each dose, 0.1 mL/10 g body weight of the suspension was administered. The compound was prepared at the highest concentration for that study and appropriate dilutions of the stock solution were made so that 0.1 mL/10 g body weight was administered. Twenty four hours later, the difference in right vs. left ear thickness was measured. The results of this experiment are presented in Table 3 below.

TABLE 3

Effect on the DTH Response to Oxazolone

| Compound | Dose (mg/kg) | Right-Left Ear (mean ± SEM) | P Value (vs. vehicle) |
|---|---|---|---|
| Vehicle only | — | 0.30 ± 0.02 | — |
| Test Cpd. | 10 (i.p.) | 0.27 ± 0.01 | 0.163 |
| Test Cpd. | 30 (i.p.) | 0.13 ± 0.02 | <0.001* |
| Cyclophosphamide | 50 (i.p.) | 0.08 ± 0.01 | <0.001 |

*One animal died during study

The test compound (30 mg/kg i.p.) and cyclophosphamide (50 mg/kg i.p.) significantly attenuated the delayed-type response to oxazolone by 56% and 73%, respectively.

It will be appreciated that, although specific embodiments of this invention have been described herein for purpose of illustration, various modifications may be made without departing from the spirit and scope of the invention.

We claim:

1. A method for treating an inflammatory condition, comprising administering to a warm-blooded animal in need thereof an effective amount of a compound having the structure:

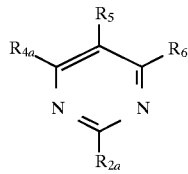

wherein $R_5$ is selected from the following chemical moieties:

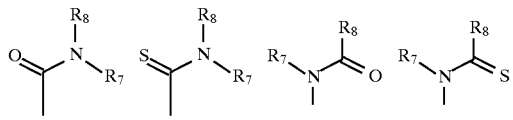

$R_7$ is selected from hydrogen, —$CH_3$, and —$CH_2C_6H_5$;

$R_8$ is selected from hydrogen and an unsubstituted or substituted $C_{1-8}$alkyl, $C_{6-12}$aryl, $C_{7-12}$ aralkyl, $C_{3-12}$heterocycle and a $C_{4-20}$ heterocyclealkyl;

$R_{2a}$ is selected from halogen, an unsubstituted or substituted $C_{1-8}$alkyl, $C_{6-12}$aryl, $C_{7-12}$aralkyl, $C_{3-12}$heterocycle or $C_{4-20}$heterocyclealkyl, —CN, —OR, —NRR and —NRNCOR;

$R_{4a}$ is selected from hydrogen, halogen, an unsubstituted or substituted $C_{1-8}$alkyl, $C_{6-12}$aryl, $C_{7-12}$aralkyl, $C_{3-12}$heterocycle or $C_{4-20}$heterocyclealkyl, —CN, —OR, —NRR and —NRNCOR; and $R_6$ is selected from hydrogen, halogen and an unsubstituted or substituted $C_{1-8}$alkyl;

and wherein each occurrence of R is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl.

2. The method of claim 1 wherein the inflammatory condition is an immunoinflammatory condition.

3. The method of claim 2 wherein the immunoinflammatory condition is selected from rheumatoid arthritis, osteoarthritis, transplant rejection, sepsis, ARDS and asthma.

4. The method of claim 2 wherein the immunoinflammatory condition is rheumatoid arthritis.

5. The method of claim 1 wherein the inflammatory condition is an autoimmune disease.

6. The method of claim 5 wherein the autoimmune disease is selected from multiple sclerosis, psoriasis, inflammatory bowel disease, glomerulonephritis, lupus, uveitis and chronic hepatitis.

7. The method of claim 1 wherein the inflammatory condition is selected from trauma, oxidative stress, cell death, irradiation damage, ischemia, reperfusion, cancer and viral infection.

8. The method of claim 1 wherein the inflammatory condition is transplant rejection.

9. The method of claim 1 wherein the compound has the structure:

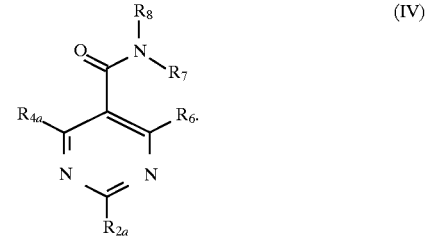

(IV)

10. The method of claim 9 wherein $R_{4a}$ is selected from —$CF_3$, —Cl, —F, —$CH_3$ and —H.

11. The method of claim 9 wherein $R_{2a}$ is selected from —Cl, —$OCH_3$, —$N(CH_3)_2$, —$CF_3$, —CN and —$NHC_6H_5$.

12. The method of claim 9 wherein $R_6$ is selected from —H, —$CF_3$, —$CH_3$ and —Cl.

13. The method of claim 9 wherein $R_7$ is selected from —H and —$CH_3$.

14. The method of claim 9 wherein $R_8$ is

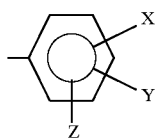

wherein X, Y and Z are the same or different, and independently selected from hydrogen, —OH, —R, —OR, —COOH, —COOR, —COR, —CONH$_2$, —NH$_2$, —NHR, —NRR, —SH, —SR, —SOOR, —SOOH and —SOR.

15. The method of claim 9 wherein $R_{4a}$ is —CF$_3$ and $R_{2a}$ is —Cl.

16. The method of claim 15 wherein the compound is selected from 2-chloro-4-trifluoromethyl-5-N-(3',5'-bistrifluoromethylphenyl)pyrimidine carboxamide; 2-chloro-4-trifluoromethyl-5-N-(3',5'-dichlorophenyl)pyrimidine carboxamide; 2-chloro-4-trifluoromethyl-5-N-(4'-trifluoromethylphenyl)pyrimidine carboxamide; 2-chloro-4-trifluoromethyl-5-N-(phenyl)pyrimidine carboxamide; 2-chloro-4-trifluoromethyl-5-N(cyclohexyl)pyrimidine carboxamide; 2-chloro-4-trifluoromethyl-5-N-(3',4',5'-trichlorophenyl)pyrimidine carboxamide; 2-chloro-4-trifluoromethyl-5-N-(benzyl)pyrimidine carboxamide; 2-chloro-4-trifluoromethyl-5-N-(4-(2',1',3'-benzothiadiazole))pyrimidine carboxamide; 2-chloro-4-trifluoromethyl-5-N-(3',5'-dichloro-6-hydroxyphenyl) pyrimidine carboxamide; 2-chloro-4-trifluoromethyl-5-N-[5-(3'-methylisoxazole)]pyrimidine carboxamide; 2-chloro-4-trifluoromethyl-5-N-(3'-N-acyl-4'-fluoroaniline) pyrimidine carboxamide; 2-chloro-4-trifluoromethyl-5-N-(3'-trifluoromethyl-5'-ethoxycarbonylphenyl)pyrimidine carboxamide; 2-chloro-4-trifluoromethyl-5-N-[3'-trifluoromethyl-5'-(carboxamide)phenyl]pyrimidine carboxamide; 2-chloro-4-trifluoromethyl-5-N-(3',5'-dichlorophenyl)-N-(methyl) pyrimidine carboxamide; and 2-chloro-4-trifluoromethyl-5-N-(3',5'-dichlorophenyl)-N-(benzyl)pyrimidine carboxamide.

17. The method of claim 9 wherein $R_{4a}$ is —CF$_3$.

18. The method of claim 17 wherein the compound is selected from 2-fluoro-4-trifluoromethyl-5-N-(3',5'-bistrifluoromethyl)pyrimidine carboxamide, 5-(3',5'-bis(trifluoromethyl)phenacyl)-2-methoxy-4-trifluoromethylpyrimidine; 4-trifluoromethyl-5N-(3',5'-dichlorophenyl)pyrimidine carboxamide; 2-dimethylamino-4-trifluoromethyl-5-N(3',5'-dichlorophenyl)pyrimidine carboxamide; 2-triethylammonium chloride-4-trifluoromethyl-5-N-(3',5'-dichlorophenyl)pyrimidine carboxamide; 2-cyano-4-trifluoromethyl-5-N-[3',5'-(bistrifluoromethyl)phenyl]pyrimidine carboxamide; 2-hydrazino4-trifluoromethyl-5-[N-(3',5'-dichlorophenyl) pyrimidine-5-carboxamide; 2-[N-(1-aminocitraconamide)]-4-trifluoromethyl-5-[N-(3',5'-dichlorophenyl) pyrimidine-5-carboxamide; and 2-aminophenyl-4-trifluoromethyl-N-(3',5'-dichlorophenyl)pyrimidine-5-carboxamide.

19. The method of claim 9 wherein $R_{2a}$ is —Cl.

20. The method of claim 19 wherein the compound selected from 5-N[3',5'-bis(trifluoromethyl)phenyl]-2,4-dichloro-6-methyl-pyrimidine carboxamide; 2-chloro4-methyl-5-N-[3',5'-(bistrifluoromethyl)phenyl]pyrimidine carboxamide; 2,4-dichloro-5-N[3',5'-bis(trifluoromethyl)benzyl]pyrimidine-5-carboxamide; and 2-chloro-4-phenyl-5-N[3',5'-(bistrifluoromethyl)phenyl]pyrimidine carboxamide.

21. The method of claim 9 wherein $R_8$ is a 3,5-disubstituted phenyl moiety, wherein both substituents are electron withdrawing groups.

22. The method of claim 21 wherein both substituents are —CF$_3$.

23. The method of claim 21 wherein at least one of the substituents is —CF$_3$.

24. The method of claim 9 wherein $R_{4a}$ is selected from —H, —CH$_3$, —CF$_3$, —CF$_2$CF$_3$, —C$_6$H$_5$ and —CH$_2$C$_6$H$_5$.

25. The method of claim 9 wherein $R_{2a}$ is selected from —Cl, —F, —CN and —CF$_3$.

26. The method of claim 9 wherein $R_{2a}$ is selected from —Cl and —F.

27. The method of claim 9 wherein $R_6$ is —H.

* * * * *